(12) United States Patent
Lentz et al.

(10) Patent No.: US 8,303,609 B2
(45) Date of Patent: Nov. 6, 2012

(54) COATED MEDICAL DEVICES

(75) Inventors: David Christian Lentz, Weston, FL (US); Gerard H. Llanos, Stewartsville, NJ (US); Mark B. Roller, North Brunswick, NJ (US); Angelo Scopelianos, Whitehouse Station, NJ (US); Kevin Weadock, Princeton, NJ (US)

(73) Assignees: Cordis Corporation; Wyeth

( * ) Notice: Subject to any disclaimer, the term of this patent is extended or adjusted under 35 U.S.C. 154(b) by 1371 days.

(21) Appl. No.: 09/966,447

(22) Filed: Sep. 28, 2001

(65) Prior Publication Data

US 2002/0133183 A1    Sep. 19, 2002

Related U.S. Application Data

(63) Continuation-in-part of application No. 09/887,464, filed on Jun. 22, 2001, now Pat. No. 7,261,735, and a continuation-in-part of application No. 09/675,882, filed on Sep. 29, 2000, now abandoned, and a continuation-in-part of application No. 09/850,482, filed on May 7, 2001, now abandoned.

(51) Int. Cl.
*A61B 17/08* (2006.01)
(52) U.S. Cl. .................................................. 606/153
(58) Field of Classification Search ................ 606/153, 606/219; 623/1.36
See application file for complete search history.

(56) References Cited

U.S. PATENT DOCUMENTS

| | | |
|---|---|---|
| 861,659 A | 7/1907 | Johnston |
| 2,357,881 A | 9/1944 | Dombrow |
| 2,424,029 A | 7/1947 | Haller |
| 2,425,753 A | 8/1947 | Mullinix |
| 3,051,677 A | 8/1962 | Rexford |
| 3,178,399 A | 4/1965 | Lo |
| 3,279,996 A | 10/1966 | Long et al. |
| 3,526,005 A | 9/1970 | Bokros |
| 3,585,707 A | 6/1971 | Stevens |
| 3,599,641 A | 8/1971 | Sheridan |
| 3,608,095 A | 9/1971 | Barry |
| 3,657,744 A | 4/1972 | Ersek |
| 3,675,647 A | 7/1972 | Pharriss et al. |
| 3,726,279 A | 4/1973 | Barefoot et al. |
| 3,744,596 A | 7/1973 | Sander |
| 3,765,414 A | 10/1973 | Arlen |

(Continued)

FOREIGN PATENT DOCUMENTS

CN    85 1 00445 A    7/1986

(Continued)

OTHER PUBLICATIONS

EPO Search Report dated Mar. 26, 2004, for corresponding EP application 03256584.

(Continued)

*Primary Examiner* — Corrine M McDermott
*Assistant Examiner* — Melissa Ryckman

(57) ABSTRACT

Medical devices, and in particular implantable medical devices, may be coated to minimize or substantially eliminate a biological organism's reaction to the introduction of the medical device to the organism. The medical devices may be coated with any number of biocompatible materials. Therapeutic drugs, agents or compounds may be mixed with the biocompatible materials and affixed to at least a portion of the medical device. These therapeutic drugs, agents or compounds may also further reduce a biological organism's reaction to the introduction of the medical device to the organism. Various materials and coating methodologies may be utilized to maintain the drugs, agents or compounds on the medical device until delivered and positioned.

1 Claim, 12 Drawing Sheets

U.S. PATENT DOCUMENTS

| | | | |
|---|---|---|---|
| 3,774,615 A | 11/1973 | Lim et al. | |
| 3,779,805 A | 12/1973 | Alsberg | |
| 3,921,636 A * | 11/1975 | Zaffaroni | 424/432 |
| 3,923,939 A * | 12/1975 | Baker et al. | 264/49 |
| 3,929,992 A | 12/1975 | Seghal et al. | |
| 3,932,627 A | 1/1976 | Margraf | |
| 3,948,254 A | 4/1976 | Zaffaroni | |
| 3,952,334 A | 4/1976 | Bokros et al. | |
| 3,952,747 A | 4/1976 | Kimmell, Jr. | |
| 3,959,078 A | 5/1976 | Guire | |
| 3,968,800 A | 7/1976 | Vilasi | |
| 3,974,526 A | 8/1976 | Dardik et al. | |
| 4,069,307 A | 1/1978 | Higuchi et al. | |
| 4,076,285 A | 2/1978 | Martinez | |
| 4,118,532 A | 10/1978 | Homsy | |
| 4,214,587 A * | 7/1980 | Sakura, Jr. | 606/155 |
| 4,252,858 A | 2/1981 | Chao et al. | |
| 4,292,965 A | 10/1981 | Nash et al. | |
| 4,299,226 A | 11/1981 | Banka | |
| 4,300,244 A | 11/1981 | Bokros | |
| 4,304,010 A | 12/1981 | Mano | |
| 4,312,920 A | 1/1982 | Pierce | |
| 4,321,711 A | 3/1982 | Mano | |
| 4,323,071 A | 4/1982 | Simpson et al. | |
| 4,350,160 A | 9/1982 | Kolesov et al. | |
| 4,366,819 A | 1/1983 | Kaster | |
| 4,368,736 A | 1/1983 | Kaster | |
| 4,390,599 A | 6/1983 | Broyles | |
| 4,413,359 A | 11/1983 | Akiyama et al. | |
| 4,423,183 A | 12/1983 | Close | |
| 4,441,216 A | 4/1984 | Ionescu et al. | |
| 4,455,690 A | 6/1984 | Homsy | |
| 4,503,569 A | 3/1985 | Dotter | |
| 4,512,338 A | 4/1985 | Balko et al. | |
| 4,550,447 A | 11/1985 | Seiler, Jr. et al. | |
| 4,553,545 A | 11/1985 | Maass et al. | |
| 4,560,374 A | 12/1985 | Hammerslag | |
| 4,562,596 A | 1/1986 | Kornberg | |
| 4,564,013 A | 1/1986 | Lilenfeld et al. | |
| 4,565,740 A | 1/1986 | Golander et al. | |
| 4,580,568 A | 4/1986 | Gianturco | |
| 4,613,665 A | 9/1986 | Larm | |
| 4,619,246 A | 10/1986 | Molgaard-Nielsen | |
| 4,624,257 A | 11/1986 | Berggren et al. | |
| 4,642,111 A | 2/1987 | Sakamoto et al. | |
| 4,655,771 A | 4/1987 | Wallsten | |
| 4,656,083 A | 4/1987 | Hoffman et al. | |
| 4,665,905 A | 5/1987 | Brown | |
| 4,676,241 A | 6/1987 | Webb et al. | |
| 4,678,466 A | 7/1987 | Rosenwald | |
| 4,687,482 A | 8/1987 | Hanson | |
| 4,688,553 A | 8/1987 | Metals | |
| 4,689,046 A | 8/1987 | Bokros | |
| 4,722,906 A | 2/1988 | Guire | |
| 4,727,873 A | 3/1988 | Mobin-Uddin | |
| 4,731,054 A | 3/1988 | Billeter et al. | |
| 4,733,665 A | 3/1988 | Palmaz | |
| 4,739,762 A | 4/1988 | Palmaz | |
| 4,740,207 A | 4/1988 | Kreamer | |
| 4,749,585 A | 6/1988 | Greco et al. | |
| 4,753,652 A | 6/1988 | Langer et al. | |
| 4,760,849 A | 8/1988 | Kropf | |
| 4,768,507 A | 9/1988 | Fischell et al. | |
| 4,776,337 A | 10/1988 | Palmaz | |
| 4,786,500 A | 11/1988 | Wong | |
| 4,787,899 A | 11/1988 | Lazarus | |
| 4,800,882 A | 1/1989 | Gianturco | |
| 4,810,784 A | 3/1989 | Larm | |
| 4,816,339 A | 3/1989 | Tu et al. | |
| 4,856,516 A | 8/1989 | Hillstead | |
| 4,871,357 A | 10/1989 | Hsu et al. | |
| 4,872,867 A | 10/1989 | Joh | |
| 4,876,109 A | 10/1989 | Mayer et al. | |
| 4,886,062 A | 12/1989 | Wiktor | |
| 4,907,336 A | 3/1990 | Gianturco | |
| 4,916,193 A | 4/1990 | Tang et al. | |
| 4,917,090 A | 4/1990 | Berggren et al. | |
| 4,917,091 A | 4/1990 | Berggren et al. | |
| 4,925,445 A | 5/1990 | Sakamoto | |
| 4,950,256 A | 8/1990 | Luther et al. | |
| 4,954,126 A | 9/1990 | Wallsten | |
| 4,969,458 A | 11/1990 | Wiktor | |
| 4,990,131 A | 2/1991 | Dardik | |
| 4,990,155 A | 2/1991 | Wilkoff | |
| 4,994,071 A | 2/1991 | MacGregor | |
| 4,994,298 A | 2/1991 | Yasuda | |
| 4,998,923 A | 3/1991 | Samson et al. | |
| 5,015,253 A | 5/1991 | MacGregor | |
| 5,019,090 A | 5/1991 | Pinchuk | |
| 5,019,096 A | 5/1991 | Fox, Jr. et al. | |
| 5,029,877 A | 7/1991 | Fedeli et al. | |
| 5,034,265 A | 7/1991 | Hoffman et al. | |
| 5,035,706 A | 7/1991 | Gianturco | |
| 5,041,100 A | 8/1991 | Rowland et al. | |
| 5,041,126 A | 8/1991 | Gianturco | |
| 5,045,072 A | 9/1991 | Castillo | |
| 5,047,020 A | 9/1991 | Hsu | |
| 5,049,132 A | 9/1991 | Shaffer et al. | |
| 5,049,403 A | 9/1991 | Larm et al. | |
| 5,053,048 A | 10/1991 | Pinchuk | |
| 5,059,166 A | 10/1991 | Fischell et al. | |
| 5,061,275 A | 10/1991 | Wallsten et al. | |
| 5,061,276 A | 10/1991 | Tu et al. | |
| 5,061,750 A | 10/1991 | Feijen et al. | |
| 5,064,435 A | 11/1991 | Porter | |
| 5,092,877 A | 3/1992 | Pinchuk | |
| 5,102,417 A | 4/1992 | Palmaz | |
| 5,104,404 A | 4/1992 | Wolff | |
| 5,108,418 A | 4/1992 | Lefebvre | |
| 5,116,365 A | 5/1992 | Hillstead | |
| 5,122,154 A | 6/1992 | Rhodes | |
| 5,123,913 A | 6/1992 | Wilk et al. | |
| 5,131,908 A | 7/1992 | Dardik et al. | |
| 5,133,732 A | 7/1992 | Wiktor | |
| 5,134,192 A | 7/1992 | Feijen et al. | |
| 5,135,536 A | 8/1992 | Hillstead | |
| 5,163,952 A | 11/1992 | Froix | |
| 5,163,958 A | 11/1992 | Pinchuk | |
| 5,392,747 A | 11/1992 | Williams et al. | |
| 5,171,217 A | 12/1992 | March et al. | |
| 5,171,262 A | 12/1992 | MacGregor | |
| 5,176,660 A | 1/1993 | Truckai | |
| 5,176,972 A | 1/1993 | Bloom et al. | |
| 5,178,618 A | 1/1993 | Kandarpa | |
| 5,180,366 A | 1/1993 | Woods | |
| 5,182,317 A | 1/1993 | Winters et al. | |
| 5,185,408 A | 2/1993 | Tang et al. | |
| 5,192,307 A | 3/1993 | Wall | |
| 5,195,984 A | 3/1993 | Schalz | |
| 5,197,977 A | 3/1993 | Hoffman, Jr. et al. | |
| 5,199,951 A | 4/1993 | Spears | |
| 5,202,332 A | 4/1993 | Hughes et al. | |
| 5,213,576 A | 5/1993 | Abiuso et al. | |
| 5,213,898 A | 5/1993 | Larm et al. | |
| 5,217,483 A | 6/1993 | Tower | |
| 5,222,971 A | 6/1993 | Willard et al. | |
| 5,226,913 A | 7/1993 | Pinchuk | |
| 5,229,172 A | 7/1993 | Cahalan et al. | |
| 5,234,160 A | 8/1993 | Lisiecki | |
| 5,234,447 A * | 8/1993 | Kaster et al. | 606/153 |
| 5,234,456 A | 8/1993 | Silvestrini | |
| 5,234,458 A | 8/1993 | Metais | |
| 5,246,445 A | 9/1993 | Yachia et al. | |
| 5,252,579 A | 10/1993 | Skotnicki et al. | |
| 5,254,107 A | 10/1993 | Soltesz | |
| 5,256,790 A | 10/1993 | Nelson | |
| 5,258,020 A | 11/1993 | Froix | |
| 5,258,021 A | 11/1993 | Duran | |
| 5,262,451 A | 11/1993 | Winters et al. | |
| 5,263,984 A | 11/1993 | Li et al. | |
| 5,266,073 A | 11/1993 | Wall | |
| 5,272,012 A | 12/1993 | Opolski | |
| 5,275,622 A | 1/1994 | Lazarus et al. | |
| 5,282,823 A | 2/1994 | Schwartz et al. | |
| 5,282,824 A | 2/1994 | Gianturco | |
| 5,283,257 A | 2/1994 | Gregory et al. | |
| 5,288,711 A | 2/1994 | Mitchell et al. | |

| | | | | | | |
|---|---|---|---|---|---|---|
| 5,290,305 | A | 3/1994 | Inoue | 5,464,540 | A | 11/1995 | Friesen et al. |
| 5,292,331 | A | 3/1994 | Boneau | 5,464,580 | A | 11/1995 | Popescu et al. |
| 5,292,802 | A | 3/1994 | Rhee et al. | 5,464,650 | A | 11/1995 | Berg et al. |
| 5,304,121 | A | 4/1994 | Sahatjian | 5,472,702 | A | 12/1995 | Muth et al. |
| 5,304,200 | A | 4/1994 | Spaulding | 5,472,985 | A | 12/1995 | Grainger et al. |
| 5,306,250 | A | 4/1994 | March et al. | 5,474,563 | A | 12/1995 | Myler et al. |
| 5,308,641 | A | 5/1994 | Cahalan et al. | 5,486,357 | A | 1/1996 | Narayanan |
| 5,308,862 | A | 5/1994 | Ohlstein | 5,491,231 | A | 2/1996 | Nelson et al. |
| 5,308,889 | A | 5/1994 | Rhee et al. | 5,496,365 | A | 3/1996 | Sgro |
| 5,311,884 | A | 5/1994 | Scopelianos | 5,500,013 | A | 3/1996 | Buscemi et al. |
| 5,314,444 | A | 5/1994 | Gianturco | 5,504,091 | A | 4/1996 | Molnar-Kimber et al. |
| 5,314,472 | A | 5/1994 | Fontaine | 5,508,286 | A | 4/1996 | Skotnicki et al. |
| 5,328,471 | A | 7/1994 | Slepian | 5,510,077 | A | 4/1996 | Dinh et al. |
| 5,334,301 | A | 8/1994 | Heinke et al. | 5,512,055 | A | 4/1996 | Domb et al. |
| 5,336,518 | A | 8/1994 | Pallassana et al. | 5,514,680 | A | 5/1996 | Weber et al. |
| 5,338,770 | A | 8/1994 | Winters et al. | 5,516,781 | A | 5/1996 | Morris et al. |
| 5,342,348 | A | 8/1994 | Kaplan | 5,519,042 | A | 5/1996 | Morris et al. |
| 5,342,387 | A | 8/1994 | Summers | 5,523,092 | A | 6/1996 | Hanson et al. |
| 5,342,621 | A | 8/1994 | Eury | 5,525,610 | A | 6/1996 | Caufield et al. |
| 5,350,800 | A | 9/1994 | Verhoeven et al. | 5,527,354 | A | 6/1996 | Fontaine et al. |
| 5,354,257 | A | 10/1994 | Roubin et al. | 5,540,928 | A | 7/1996 | Edelman et al. |
| 5,354,308 | A | 10/1994 | Simon et al. | 5,541,191 | A | 7/1996 | Skotnicki et al. |
| 5,356,433 | A | 10/1994 | Rowland et al. | 5,545,208 | A | 8/1996 | Wolff et al. |
| 5,362,718 | A | 11/1994 | Skotnicki et al. | 5,551,954 | A | 9/1996 | Buscemi et al. |
| 5,365,668 | A | 11/1994 | Canovas | 5,554,182 | A | 9/1996 | Dinh et al. |
| 5,366,504 | A | 11/1994 | Andersen et al. | 5,554,954 | A | 9/1996 | Takahashi |
| 5,367,023 | A | 11/1994 | Caporiccio et al. | 5,556,413 | A | 9/1996 | Lam |
| 5,368,566 | A | 11/1994 | Crocker | 5,559,122 | A | 9/1996 | Nelson et al. |
| 5,370,683 | A | 12/1994 | Fontaine | 5,562,922 | A | 10/1996 | Lambert |
| 5,370,691 | A | 12/1994 | Samson | 5,563,145 | A | 10/1996 | Failli et al. |
| 5,375,612 | A | 12/1994 | Cottenceau et al. | 5,563,146 | A | 10/1996 | Morris et al. |
| 5,376,112 | A | 12/1994 | Duran | 5,569,197 | A | 10/1996 | Helmus et al. |
| 5,378,475 | A | 1/1995 | Smith et al. | 5,569,295 | A | 10/1996 | Lam |
| 5,378,836 | A | 1/1995 | Kao et al. | 5,569,462 | A | 10/1996 | Martinson et al. |
| 5,380,299 | A | 1/1995 | Fearnot et al. | 5,569,463 | A | 10/1996 | Helmus et al. |
| 5,382,261 | A | 1/1995 | Palmaz | 5,571,089 | A | 11/1996 | Crocker |
| 5,383,853 | A | 1/1995 | Jung et al. | 5,571,166 | A | 11/1996 | Dinh et al. |
| 5,383,887 | A | 1/1995 | Nadal | 5,571,191 | A | 11/1996 | Fitz |
| 5,383,928 | A | 1/1995 | Scott et al. | 5,574,059 | A | 11/1996 | Regunathan et al. |
| 5,385,908 | A | 1/1995 | Nelson et al. | 5,575,818 | A | 11/1996 | Pinchuk |
| 5,385,909 | A | 1/1995 | Nelson et al. | 5,578,075 | A | 11/1996 | Dayton |
| 5,385,910 | A | 1/1995 | Ocain et al. | 5,580,873 | A | 12/1996 | Bianco et al. |
| 5,387,235 | A | 2/1995 | Chuter | 5,580,874 | A | 12/1996 | Bianco et al. |
| 5,387,680 | A | 2/1995 | Nelson | 5,584,877 | A | 12/1996 | Miyake et al. |
| 5,389,106 | A | 2/1995 | Tower | 5,591,140 | A | 1/1997 | Narayanan et al. |
| 5,389,639 | A | 2/1995 | Failli et al. | 5,591,197 | A | 1/1997 | Orth et al. |
| 5,391,730 | A | 2/1995 | Skotnicki et al. | 5,591,224 | A | 1/1997 | Schwartz et al. |
| 5,393,772 | A | 2/1995 | Yue et al. | 5,591,227 | A | 1/1997 | Dinh et al. |
| 5,395,390 | A | 3/1995 | Simon et al. | 5,599,352 | A | 2/1997 | Dinh et al. |
| 5,397,355 | A | 3/1995 | Marin et al. | 5,599,844 | A | 2/1997 | Grainger et al. |
| 5,399,352 | A | 3/1995 | Hanson | 5,603,722 | A | 2/1997 | Phan et al. |
| 5,403,341 | A | 4/1995 | Solar | 5,603,894 | A | 2/1997 | Aikus et al. |
| 5,405,377 | A | 4/1995 | Cragg | 5,604,283 | A | 2/1997 | Wada et al. |
| 5,409,696 | A | 4/1995 | Narayanan et al. | 5,605,696 | A | 2/1997 | Eury et al. |
| 5,411,549 | A | 5/1995 | Peters | 5,607,463 | A | 3/1997 | Schwartz et al. |
| 5,415,619 | A | 5/1995 | Lee et al. | 5,607,475 | A | 3/1997 | Cahalan et al. |
| 5,415,938 | A | 5/1995 | Cahalan et al. | 5,609,629 | A | 3/1997 | Fearnot et al. |
| 5,417,969 | A | 5/1995 | Hsu et al. | 5,616,608 | A | 4/1997 | Kinsella et al. |
| 5,419,760 | A | 5/1995 | Narciso, Jr. | 5,618,837 | A | 4/1997 | Hart et al. |
| D359,802 | S | 6/1995 | Fontaine | 5,620,984 | A | 4/1997 | Bianco et al. |
| 5,421,955 | A | 6/1995 | Lau | 5,621,102 | A | 4/1997 | Bianco et al. |
| 5,423,885 | A | 6/1995 | Williams | 5,622,975 | A | 4/1997 | Singh et al. |
| 5,429,618 | A | 7/1995 | Keogh | 5,624,411 | A * | 4/1997 | Tuch ............................ 604/265 |
| 5,429,634 | A | 7/1995 | Narciso | 5,628,756 | A | 5/1997 | Barker, Jr. et al. |
| 5,439,446 | A | 8/1995 | Barry | 5,628,785 | A | 5/1997 | Schwartz et al. |
| 5,441,515 | A | 8/1995 | Khosravi et al. | 5,628,786 | A | 5/1997 | Banas et al. |
| 5,441,516 | A | 8/1995 | Wang et al. | 5,629,077 | A | 5/1997 | Turnlund et al. |
| 5,441,947 | A | 8/1995 | Dodge et al. | 5,629,315 | A | 5/1997 | Bianco et al. |
| 5,441,977 | A | 8/1995 | Russo et al. | 5,632,763 | A | 5/1997 | Glastra |
| 5,443,458 | A | 8/1995 | Eury | 5,632,771 | A | 5/1997 | Boatman et al. |
| 5,443,477 | A | 8/1995 | Marin et al. | 5,632,776 | A | 5/1997 | Kurumatani et al. |
| 5,443,496 | A | 8/1995 | Schwartz et al. | 5,632,840 | A | 5/1997 | Campbell |
| 5,443,498 | A | 8/1995 | Fontaine | 5,635,201 | A | 6/1997 | Fabo |
| 5,443,500 | A | 8/1995 | Sigwart | 5,637,113 | A | 6/1997 | Tartaglia et al. |
| 5,447,724 | A | 9/1995 | Heimus et al. | 5,643,312 | A | 7/1997 | Fischell et al. |
| 5,449,372 | A | 9/1995 | Schmaltz et al. | 5,643,939 | A | 7/1997 | Ohlstein |
| 5,449,373 | A | 9/1995 | Pinchasik et al. | 5,646,160 | A | 7/1997 | Morris et al. |
| 5,449,382 | A | 9/1995 | Dayton | 5,648,357 | A | 7/1997 | Bianco et al. |
| 5,464,450 | A | 11/1995 | Buscemi et al. | 5,649,952 | A | 7/1997 | Lam |

| | | | | | |
|---|---|---|---|---|---|
| 5,649,977 A | 7/1997 | Campbell | 5,827,324 A | 10/1998 | Cassell et al. |
| 5,651,174 A | 7/1997 | Schwartz et al. | 5,827,587 A | 10/1998 | Fukushi |
| 5,652,243 A | 7/1997 | Bianco et al. | 5,827,734 A | 10/1998 | Weigle et al. |
| 5,653,747 A | 8/1997 | Dereume | 5,833,651 A | 11/1998 | Donovan et al. |
| 5,653,992 A | 8/1997 | Bezwada et al. | 5,836,969 A | 11/1998 | Kim et al. |
| 5,660,873 A | 8/1997 | Nikolaychik et al. | 5,837,008 A | 11/1998 | Berg et al. |
| 5,662,609 A | 9/1997 | Slepian | 5,837,313 A | 11/1998 | Ding et al. |
| 5,662,712 A | 9/1997 | Pathak et al. | 5,843,120 A | 12/1998 | Israel et al. |
| 5,665,591 A | 9/1997 | Sonenshein et al. | 5,843,166 A | 12/1998 | Lentz et al. |
| 5,665,728 A | 9/1997 | Morris et al. | 5,843,172 A | 12/1998 | Yan |
| 5,665,772 A | 9/1997 | Cottens et al. | 5,849,034 A | 12/1998 | Schwartz |
| 5,667,523 A | 9/1997 | Bynon et al. | 5,851,217 A | 12/1998 | Wolff et al. |
| 5,667,764 A | 9/1997 | Kopia et al. | 5,851,231 A | 12/1998 | Wolff et al. |
| 5,669,924 A | 9/1997 | Shaknovich | 5,858,967 A | 1/1999 | Weigle et al. |
| 5,670,506 A | 9/1997 | Leigh et al. | 5,858,990 A | 1/1999 | Walsh |
| 5,672,638 A | 9/1997 | Verhoeven et al. | 5,861,027 A | 1/1999 | Trapp |
| 5,674,242 A | 10/1997 | Phan et al. | 5,865,814 A | 2/1999 | Tuch |
| 5,676,670 A | 10/1997 | Kim | 5,868,763 A | 2/1999 | Spence et al. |
| 5,679,400 A | 10/1997 | Tuch | 5,871,535 A | 2/1999 | Wolff et al. |
| 5,679,659 A | 10/1997 | Verhoeven et al. | 5,873,904 A | 2/1999 | Ragheb et al. |
| 5,684,061 A | 11/1997 | Ohnishi et al. | 5,876,433 A | 3/1999 | Lunn |
| 5,691,311 A | 11/1997 | Maraganore et al. | 5,876,449 A | 3/1999 | Starck et al. |
| 5,693,085 A | 12/1997 | Buirge et al. | 5,877,224 A | 3/1999 | Brocchini et al. |
| 5,695,504 A | 12/1997 | Gifford, III | 5,879,697 A | 3/1999 | Ding et al. |
| 5,697,967 A | 12/1997 | Dinh et al. | 5,882,335 A | 3/1999 | Leone et al. |
| 5,697,971 A | 12/1997 | Fischell et al. | 5,883,110 A | 3/1999 | Tang et al. |
| 5,700,286 A | 12/1997 | Tartaglia et al. | 5,891,108 A | 4/1999 | Leone et al. |
| 5,702,669 A | 12/1997 | Green | 5,893,840 A | 4/1999 | Hull et al. |
| 5,702,699 A | 12/1997 | Hanisch | 5,897,911 A | 4/1999 | Loeffler |
| 5,707,385 A | 1/1998 | Williams | 5,900,246 A | 5/1999 | Lambert |
| 5,709,874 A | 1/1998 | Hanson et al. | 5,902,266 A | 5/1999 | Leone et al. |
| 5,710,174 A | 1/1998 | West et al. | 5,904,697 A * | 5/1999 | Gifford et al. ................. 606/155 |
| 5,713,949 A | 2/1998 | Jayaraman | 5,912,253 A | 6/1999 | Cottens et al. |
| 5,716,981 A | 2/1998 | Hunter et al. | 5,916,224 A | 6/1999 | Esplin |
| 5,720,776 A | 2/1998 | Chuter et al. | 5,916,910 A | 6/1999 | Lai |
| 5,722,982 A | 3/1998 | Ferreira et al. | 5,922,022 A | 7/1999 | Nash |
| 5,725,549 A | 3/1998 | Lam | 5,922,393 A | 7/1999 | Jayaraman |
| 5,725,567 A | 3/1998 | Wolff et al. | 5,922,730 A | 7/1999 | Hu et al. |
| 5,725,572 A | 3/1998 | Lam | 5,924,997 A | 7/1999 | Campbell |
| 5,728,150 A | 3/1998 | McDonald et al. | 5,928,279 A * | 7/1999 | Shannon et al. .............. 623/1.13 |
| 5,728,420 A | 3/1998 | Keogh | 5,932,243 A | 8/1999 | Fricker et al. |
| 5,731,326 A | 3/1998 | Hart et al. | 5,932,299 A | 8/1999 | Katoot |
| 5,733,327 A | 3/1998 | Igaki et al. | 5,932,580 A | 8/1999 | Levitzki et al. |
| 5,733,920 A | 3/1998 | Mansuri et al. | 5,951,586 A | 9/1999 | Berg et al. |
| 5,733,925 A | 3/1998 | Kunz et al. | 5,957,971 A | 9/1999 | Schwartz |
| 5,735,897 A | 4/1998 | Buirge | 5,959,075 A | 9/1999 | Lok et al. |
| 5,739,138 A | 4/1998 | Bianco et al. | 5,962,265 A | 10/1999 | Norris et al. |
| 5,741,327 A | 4/1998 | Frantzen | 5,962,516 A | 10/1999 | Qi et al. |
| 5,744,587 A | 4/1998 | Alaska et al. | 5,968,091 A | 10/1999 | Pinchuk et al. |
| 5,749,203 A | 5/1998 | McGowan, Jr. | 5,972,024 A | 10/1999 | Northrup et al. |
| 5,755,734 A | 5/1998 | Richter et al. | 5,972,027 A | 10/1999 | Johnson |
| 5,755,772 A | 5/1998 | Evans et al. | 5,976,172 A | 11/1999 | Homsma et al. |
| 5,759,205 A | 6/1998 | Valentini | 5,976,534 A | 11/1999 | Hart et al. |
| 5,769,883 A | 6/1998 | Buscemi et al. | 5,977,163 A | 11/1999 | Li et al. |
| 5,769,887 A | 6/1998 | Brown et al. | 5,980,553 A | 11/1999 | Gray et al. |
| 5,776,184 A | 7/1998 | Tuch | 5,980,566 A | 11/1999 | Alt et al. |
| 5,780,462 A | 7/1998 | Lee et al. | 5,980,972 A | 11/1999 | Ding |
| 5,780,476 A | 7/1998 | Underiner et al. | 5,981,568 A | 11/1999 | Kunz et al. |
| 5,782,908 A | 7/1998 | Cahalan et al. | 5,985,307 A | 11/1999 | Hanson et al. |
| 5,786,171 A | 7/1998 | Lee et al. | 5,986,049 A | 11/1999 | Forstrom et al. |
| 5,788,979 A | 8/1998 | Alt | 5,997,468 A | 12/1999 | Wolff et al. |
| 5,792,106 A | 8/1998 | Mische | 6,001,118 A | 12/1999 | Daniel et al. |
| 5,792,772 A | 8/1998 | Bianco et al. | 6,004,346 A | 12/1999 | Wolff et al. |
| 5,798,372 A | 8/1998 | Davies et al. | 6,011,082 A | 1/2000 | Wang et al. |
| 5,799,384 A | 9/1998 | Schwartz et al. | 6,015,432 A * | 1/2000 | Rakos et al. ................. 623/1.13 |
| 5,800,507 A | 9/1998 | Schwartz | 6,015,815 A | 1/2000 | Mollison |
| 5,800,508 A | 9/1998 | Goicoechea et al. | 6,022,374 A | 2/2000 | Imran |
| 5,800,525 A | 9/1998 | Bachinski et al. | 6,025,414 A | 2/2000 | Rich |
| 5,800,526 A | 9/1998 | Anderson | 6,030,663 A | 2/2000 | McClain et al. |
| 5,807,743 A | 9/1998 | Stinchcomb et al. | 6,039,721 A | 3/2000 | Johnson et al. |
| 5,807,861 A | 9/1998 | Klein et al. | 6,059,813 A | 5/2000 | Vrba et al. |
| 5,811,447 A | 9/1998 | Kunz et al. | 6,071,305 A | 6/2000 | Brown et al. |
| 5,814,064 A | 9/1998 | Daniel et al. | 6,074,659 A | 6/2000 | Kunz et al. |
| 5,820,917 A | 10/1998 | Tuch | 6,080,190 A | 6/2000 | Schwartz |
| 5,820,918 A | 10/1998 | Ronan et al. | 6,096,070 A | 8/2000 | Ragheb et al. |
| 5,822,601 A | 10/1998 | DeRoo et al. | 6,099,549 A | 8/2000 | Bosma et al. |
| 5,824,042 A | 10/1998 | Lombardi et al. | 6,099,562 A | 8/2000 | Ding et al. |
| 5,824,048 A | 10/1998 | Tuch | 6,099,652 A | 8/2000 | Patten, Jr. et al. |
| 5,824,049 A | 10/1998 | Ragheb et al. | 6,110,188 A | 8/2000 | Narciso, Jr. |

| | | | |
|---|---|---|---|
| 6,113,612 A * | 9/2000 | Swanson et al. ............. 623/1.15 |
| 6,117,147 A | 9/2000 | Simpson et al. |
| 6,120,536 A | 9/2000 | Dinge et al. |
| 6,120,847 A | 9/2000 | Yang et al. |
| 6,129,754 A | 10/2000 | Kanesaka et al. |
| 6,129,755 A | 10/2000 | Mathis et al. |
| 6,136,798 A | 10/2000 | Cody et al. |
| 6,140,127 A | 10/2000 | Sprague |
| 6,143,354 A | 11/2000 | Koulik et al. |
| 6,146,358 A | 11/2000 | Rowe |
| 6,152,946 A | 11/2000 | Broome et al. |
| 6,153,252 A | 11/2000 | Hossainy |
| 6,159,488 A | 12/2000 | Nagler et al. |
| 6,165,185 A | 12/2000 | Shennib |
| 6,165,559 A | 12/2000 | McClain et al. |
| 6,168,604 B1 | 1/2001 | Cano |
| 6,171,232 B1 | 1/2001 | Papandreou et al. |
| 6,171,609 B1 | 1/2001 | Kunz |
| 6,177,272 B1 | 1/2001 | Nabel et al. |
| 6,179,817 B1 | 1/2001 | Zhong |
| 6,179,861 B1 | 1/2001 | Khosravi et al. |
| 6,179,864 B1 | 1/2001 | Peters-Combs |
| 6,187,757 B1 | 2/2001 | Clackson et al. |
| 6,190,403 B1 | 2/2001 | Fischell et al. |
| 6,193,746 B1 | 2/2001 | Strecker |
| 8,187,038 B2 | 2/2001 | Sullivan et al. |
| 6,203,569 B1 | 3/2001 | Wijay |
| 6,214,040 B1 | 4/2001 | Jayaraman |
| 6,214,901 B1 | 4/2001 | Chudzik et al. |
| 6,225,346 B1 | 5/2001 | Tang et al. |
| 6,231,598 B1 | 5/2001 | Berry et al. |
| 6,238,687 B1 | 5/2001 | Mao |
| 6,240,616 B1 | 6/2001 | Yan |
| 6,245,012 B1 | 6/2001 | Kleshinski |
| 6,245,026 B1 | 6/2001 | Campbell et al. |
| 6,245,100 B1 | 6/2001 | Davβa et al. |
| 6,245,537 B1 | 6/2001 | Williams et al. |
| 6,251,920 B1 | 6/2001 | Grainger et al. |
| 6,254,618 B1 | 7/2001 | Dakov |
| 6,254,632 B1 | 7/2001 | Wu et al. |
| 6,254,634 B1 | 7/2001 | Anderson et al. |
| 6,258,121 B1 | 7/2001 | Yang et al. |
| 6,268,390 B1 | 7/2001 | Kunz |
| 6,273,913 B1 | 8/2001 | Wright et al. |
| 6,284,305 B1 | 9/2001 | Ding et al. |
| 6,287,320 B1 | 9/2001 | Slepian |
| 6,287,628 B1 | 9/2001 | Hossainy et al. |
| 6,293,966 B1 | 9/2001 | Frantzen |
| 6,299,604 B1 | 10/2001 | Ragheb et al. |
| 6,306,144 B1 | 10/2001 | Sydney et al. |
| 6,306,166 B1 | 10/2001 | Barry et al. |
| 6,306,421 B1 | 10/2001 | Kunz et al. |
| 6,308,176 B1 | 10/2001 | Whitbourne |
| 6,309,380 B1 | 10/2001 | Larson et al. |
| 6,309,660 B1 | 10/2001 | Hsu et al. |
| 6,313,264 B1 | 11/2001 | Caggiano et al. |
| 6,315,790 B1 | 11/2001 | Gerberding et al. |
| 6,316,018 B1 | 11/2001 | Ding et al. |
| 6,334,871 B1 | 1/2002 | Dor et al. |
| 6,335,029 B1 | 1/2002 | Kamath et al. |
| 6,348,064 B1 * | 2/2002 | Kanner ................. 606/219 |
| 6,358,556 B1 | 3/2002 | Ding et al. |
| 6,361,559 B1 | 3/2002 | Houser et al. |
| 6,368,658 B1 | 4/2002 | Schwarz et al. |
| 6,369,039 B1 | 4/2002 | Palasis et al. |
| 6,371,964 B1 | 4/2002 | Vargas et al. |
| 6,375,676 B1 | 4/2002 | Cox |
| 6,379,382 B1 | 4/2002 | Yang |
| 6,384,046 B1 | 5/2002 | Schuler et al. |
| 6,387,121 B1 | 5/2002 | Alt |
| 6,402,777 B1 | 6/2002 | Globerman et al. |
| 6,403,635 B1 | 6/2002 | Kinsella et al. |
| 6,407,067 B1 | 6/2002 | Schafer |
| 6,425,898 B1 | 7/2002 | Wilson et al. |
| 6,429,232 B1 | 8/2002 | Kinsella et al. |
| 6,448,221 B1 | 9/2002 | Sheppard et al. |
| 6,458,140 B2 | 10/2002 | Akin et al. |
| 6,471,979 B2 | 10/2002 | New et al. |
| 6,471,980 B2 | 10/2002 | Sirhan et al. |
| 6,485,496 B1 | 11/2002 | Suyker et al. |
| 6,517,573 B1 | 2/2003 | Pollock et al. |
| 6,517,858 B1 | 2/2003 | Le Moel |
| 6,517,889 B1 | 2/2003 | Jayaraman |
| 6,545,097 B2 | 4/2003 | Pinchuk et al. |
| 6,565,581 B1 | 5/2003 | Spence et al. |
| 6,585,764 B2 | 7/2003 | Wright et al. |
| 6,599,302 B2 | 7/2003 | Houser et al. |
| 6,602,287 B1 | 8/2003 | Millare et al. |
| 6,607,541 B1 | 8/2003 | Gardiner et al. |
| 6,613,084 B2 | 9/2003 | Yang |
| 6,620,194 B2 | 9/2003 | Ding et al. |
| 6,623,521 B2 | 9/2003 | Steinke et al. |
| 6,626,920 B2 | 9/2003 | Whayne |
| 6,627,246 B2 | 9/2003 | Mehta et al. |
| 6,641,593 B1 | 11/2003 | Schaller et al. |
| 6,648,901 B2 | 11/2003 | Fleischman et al. |
| 6,656,216 B1 | 12/2003 | Hossainy et al. |
| 6,663,606 B1 | 12/2003 | Barry et al. |
| 6,673,385 B1 | 1/2004 | Ding et al. |
| 6,713,119 B2 | 3/2004 | Hossainy et al. |
| 6,730,103 B2 | 5/2004 | Dakov |
| 6,746,773 B2 | 6/2004 | Llanos et al. |
| 6,753,071 B1 | 6/2004 | Pacetti |
| 6,776,796 B2 | 8/2004 | Llanos et al. |
| 6,787,179 B2 | 9/2004 | Timm et al. |
| 6,808,536 B2 | 10/2004 | Wright et al. |
| 6,818,247 B1 | 11/2004 | Chen et al. |
| 6,833,153 B1 | 12/2004 | Roorda et al. |
| 6,852,122 B2 | 2/2005 | Rush |
| 6,872,225 B1 | 3/2005 | Rowan et al. |
| 6,919,100 B2 | 7/2005 | Narayanan |
| 6,939,375 B2 | 9/2005 | Sirhan et al. |
| 6,962,595 B1 | 11/2005 | Chamness et al. |
| 7,018,405 B2 | 3/2006 | Sirhan et al. |
| 7,048,939 B2 | 5/2006 | Elkins et al. |
| 7,056,339 B2 | 6/2006 | Elkins et al. |
| 7,056,550 B2 | 6/2006 | Davila et al. |
| 7,087,078 B2 | 8/2006 | Hildebrand et al. |
| 7,135,039 B2 | 11/2006 | De Scheerder et al. |
| 7,186,518 B2 | 3/2007 | Wang et al. |
| 7,195,640 B2 | 3/2007 | Falotico et al. |
| 7,223,286 B2 | 5/2007 | Wright et al. |
| 7,300,662 B2 | 11/2007 | Falotico et al. |
| 7,591,844 B2 | 9/2009 | Llanos et al. |
| 2001/0007083 A1 | 7/2001 | Roorda |
| 2001/0029351 A1 | 10/2001 | Falotico et al. |
| 2001/0029660 A1 | 10/2001 | Johnson |
| 2001/0032014 A1 | 10/2001 | Yang et al. |
| 2001/0034363 A1 | 10/2001 | Li et al. |
| 2001/0037145 A1 | 11/2001 | Guruwaiya et al. |
| 2001/0053931 A1 | 12/2001 | Hess et al. |
| 2002/0010418 A1 | 1/2002 | Lary et al. |
| 2002/0013591 A1 | 1/2002 | Campbell et al. |
| 2002/0032477 A1 | 3/2002 | Helmus et al. |
| 2002/0041899 A1 | 4/2002 | Chudzik et al. |
| 2002/0051730 A1 | 5/2002 | Bodnar et al. |
| 2002/0058984 A1 | 5/2002 | Solovay et al. |
| 2002/0061326 A1 | 5/2002 | Li et al. |
| 2002/0065557 A1 | 5/2002 | Goble et al. |
| 2002/0068969 A1 | 6/2002 | Shanley et al. |
| 2002/0071902 A1 | 6/2002 | Ding et al. |
| 2002/0082680 A1 | 6/2002 | Shanley et al. |
| 2002/0082685 A1 | 6/2002 | Sirhan et al. |
| 2002/0091433 A1 | 7/2002 | Ding et al. |
| 2002/0095114 A1 | 7/2002 | Palasis |
| 2002/0099394 A1 | 7/2002 | Houser et al. |
| 2002/0099438 A1 | 7/2002 | Furst |
| 2002/0103526 A1 | 8/2002 | Steinke |
| 2002/0111590 A1 | 8/2002 | Davila et al. |
| 2002/0116018 A1 | 8/2002 | Stevens et al. |
| 2002/0119178 A1 | 8/2002 | Levesque et al. |
| 2002/0123505 A1 | 9/2002 | Mollison et al. |
| 2002/0127327 A1 | 9/2002 | Schwarz et al. |
| 2002/0133183 A1 | 9/2002 | Lentz et al. |
| 2002/0133222 A1 | 9/2002 | Das |
| 2002/0133224 A1 | 9/2002 | Bajgar et al. |
| 2002/0165608 A1 | 11/2002 | Llanos |
| 2002/0173803 A1 | 11/2002 | Ainsworth et al. |

| | | | |
|---|---|---|---|
| 2002/0193475 A1 | 12/2002 | Hossainy et al. | |
| 2003/0060877 A1 | 3/2003 | Falotico et al. | |
| 2003/0065377 A1 | 4/2003 | Davila et al. | |
| 2003/0204168 A1 | 10/2003 | Bosma | |
| 2003/0216699 A1 | 11/2003 | Falotico | |
| 2004/0049265 A1 | 3/2004 | Ding et al. | |
| 2004/0102758 A1 | 5/2004 | Davila et al. | |
| 2004/0243097 A1 | 12/2004 | Falotico et al. | |
| 2004/0260268 A1 | 12/2004 | Falotico et al. | |
| 2005/0002986 A1 | 1/2005 | Falotico et al. | |
| 2005/0004663 A1 | 1/2005 | Llanos et al. | |
| 2005/0033261 A1 | 2/2005 | Falotico et al. | |
| 2005/0106210 A1 | 5/2005 | Ding et al. | |
| 2005/0187611 A1 | 8/2005 | Ding et al. | |
| 2005/0208200 A1 | 9/2005 | Ding et al. | |
| 2006/0088654 A1 | 4/2006 | Ding et al. | |
| 2006/0089705 A1 | 4/2006 | Ding et al. | |
| 2006/0222756 A1 | 10/2006 | Davila et al. | |
| 2006/0235503 A1 | 10/2006 | Llanos et al. | |
| 2007/0179594 A1 | 8/2007 | Llanos et al. | |
| 2007/0179595 A1 | 8/2007 | Davila et al. | |
| 2007/0179596 A1 | 8/2007 | Davila et al. | |
| 2007/0179597 A1 | 8/2007 | Davila et al. | |
| 2007/0276473 A1 | 11/2007 | Llanos et al. | |
| 2007/0276474 A1 | 11/2007 | Llanos et al. | |
| 2007/0276475 A1 | 11/2007 | Llanos et al. | |
| 2007/0276476 A1 | 11/2007 | Llanos et al. | |
| 2008/0051883 A1 | 2/2008 | Llanos et al. | |
| 2008/0051884 A1 | 2/2008 | Llanos et al. | |
| 2008/0051885 A1 | 2/2008 | Llanos et al. | |

FOREIGN PATENT DOCUMENTS

| | | |
|---|---|---|
| CN | 85 1 00493 A | 8/1986 |
| DE | 3205942 A1 | 9/1983 |
| DE | 197 23 723 A | 12/1998 |
| DE | 20112123 | 10/2001 |
| EP | 540290 A2 | 10/1992 |
| EP | 0 568 310 A1 | 11/1993 |
| EP | 604 022 A1 | 6/1994 |
| EP | 621 015 A1 | 10/1994 |
| EP | 623 354 A1 | 11/1994 |
| EP | 0 633 032 A | 1/1995 |
| EP | 0 633 032 A1 | 1/1995 |
| EP | 734698 A2 | 3/1996 |
| EP | 0 712 615 | 5/1996 |
| EP | 0 716 836 | 6/1996 |
| EP | 716 836 A1 | 6/1996 |
| EP | 800801 A1 | 8/1996 |
| EP | 734 721 A2 | 10/1996 |
| EP | 0 747 069 A2 | 12/1996 |
| EP | 0 761 251 | 3/1997 |
| EP | 830853 A1 | 7/1997 |
| EP | 0 815 803 A | 1/1998 |
| EP | 0 850 651 | 7/1998 |
| EP | 0 938 878 A2 | 9/1999 |
| EP | 0 938 878 A3 | 9/1999 |
| EP | 0 950 386 A2 | 10/1999 |
| EP | 0950386 B1 | 10/1999 |
| EP | 0 968 688 A | 1/2000 |
| EP | 1 040 840 A1 | 10/2000 |
| EP | 1 192 957 A | 4/2002 |
| FR | 0 566 807 A1 | 4/1992 |
| FR | 2785812 A1 | 11/1998 |
| GB | 0 662 307 A2 | 12/1951 |
| GB | 1 205 743 | 9/1970 |
| JP | 5-305092 | 11/1993 |
| JP | 2000237289 A | 9/2000 |
| JP | 01-506176 A | 5/2001 |
| WO | WO 91/12779 A1 | 9/1991 |
| WO | WO 92/15286 A1 | 9/1992 |
| WO | WO 94/01056 A1 | 1/1994 |
| WO | WO 94/21308 A1 | 9/1994 |
| WO | WO 94/21309 A1 | 9/1994 |
| WO | WO 94/24961 A1 | 11/1994 |
| WO | WO 96/00093 A1 | 1/1996 |
| WO | WO 96/00272 A1 | 1/1996 |
| WO | WO 96/26689 B1 | 9/1996 |
| WO | WO 96/32907 | 10/1996 |
| WO | WO 96/34580 | 11/1996 |
| WO | WO 97/25000 A1 | 7/1997 |
| WO | WO 97/33534 A1 | 9/1997 |
| WO | WO 97/35575 A1 | 10/1997 |
| WO | WO 98 08463 A | 3/1998 |
| WO | WO 98/19628 | 5/1998 |
| WO | WO 98/23228 | 6/1998 |
| WO | WO 98/34669 | 8/1998 |
| WO | WO 9838784 A1 | 8/1998 |
| WO | WO 98/38687 A1 | 9/1998 |
| WO | WO 98/47447 A1 | 10/1998 |
| WO | WO 98/56312 A1 | 12/1998 |
| WO | WO 9921491 A1 | 5/1999 |
| WO | WO 99/45852 A | 9/1999 |
| WO | WO 00/24339 A | 5/2000 |
| WO | WO 00/27441 A1 | 5/2000 |
| WO | WO 0027445 A1 | 5/2000 |
| WO | WO 00 38754 A | 7/2000 |
| WO | WO 00/53126 A1 | 9/2000 |
| WO | WO 01/87342 A2 | 11/2001 |
| WO | WO 01/87375 A | 11/2001 |
| WO | WO 01/87376 A1 | 11/2001 |
| WO | WO 02/26139 A | 4/2002 |
| WO | WO 02 28281 A | 4/2002 |
| WO | WO 02/065954 A1 | 8/2002 |
| WO | WO 02/067793 A2 | 9/2002 |

OTHER PUBLICATIONS

Chinese Official Action dated May 21, 2004, for corresponding CN application 01819649.7.

Encyclopedia of Polymer Science and Engineering, vol. 7 "Fluorocarbon Elastomers" (Mar. 1989) pp. 257-267.

Verweire et al, "Evaluation of Fluorinated Polymers as Coronary Stent Coating", Journal of Materials Science: Materials in Medicine 11 (Apr. 2000).

Chinese Official Action dated May 21, 2004, for corresponding CN application 01819649.7 (with English language translation).

EPO Search Report dated Feb. 25, 2004 for EPO Appl. No. EP 03 25 6585.

EPO Search Report dated Dec. 12, 2003 for EPO Appl. No. EP 03 25 4747.

EPO Search Report dated Jan. 8, 2004 for EPO Appl. No. EP 01 30 8349.

European Search Report dated Sep. 16, 2003 for corresponding Appln. No. EP 03 25 2701.

PCT International Search Report, PCT/US01/30431, Mar. 4, 2002.

Ajroldi, G. et al., "Fluoroelastomers-Dependence of Relaxation Phenomena on Compositions", Polymer, 30, No. 12, (1989): 2180-2187.

Berk, B.C. et al., "Pharmacologic Roles of Heparin and Glucocorticoids to Prevent Restenosis After Coronary Angioplasty", J. Am. Coll. Cardio. vol. 17, No. 6, pp. 111B-117B (1991).

Campbell and Campbell, "Phenotypic Modulation of Smooth Muscle Cells in Primary Culture", (Table of Contents), Chapter 2, vol. 1, pp. 39-52 (1985).

Campbell and Campbell "Cell Biology of Smooth Muscle in Culture: Implications for Atherogenesis", Inter. Angio, 6, p. 73 (1987).

Chang, M.W. et al., "Adenovirus-mediated Over-expression of the Cyclin/Cyclin-Dependent Kinase Inhibitor, p21 Inhibits Vascular Smooth Muscle Cell Proliferation and Neointima Formation in the Rat Carotid Artery Model of Balloon Angioplasty", J. Clin. Invest. vol. 96, pp. 2260-2268 (1995).

Clowes, A.W. et al., "Suppression by Heparin of Smooth Muscle Cell Proliferation in Injured Arteries", Nature, vol. 265, pp. 625-626 (1977).

Clowes, A.W. et al., "Kinetics of Cellular Proliferation after Arterial Injury", Laboratory Investigation, vol. 52, No. 6, pp. 611-616 (1985).

Clowes, A.W. et al., "Kinetics of Cellular Proliferation after Arterial Injury IV. Heparin Inhibits Rat Smooth Muscle Mitogenesis and Migration", Circulation Research, vol. 58, No. 6, pp. 839-845 (1986).

Clowes and Schwartz, "Significance of Quiescent Smooth Muscle Migration in the Injured Rat Carotid Artery", Cir. Res. 56: 139-145 (1985).

Colburn, M.D. et al., "Dose Responsive Suppression of Myointimal Hyperplasia by Dexamethasone", J. Vasc. Surg. vol. 15, No. 3, pp. 510-518 (1992).

Currier, J.W. et al., "Colchicine Inhibits Restenosis After Iliac Angioplasty in the Atherosclerotic Rabbit", Supplement II Circulation vol. 80, No. 4, II-66 (1989).

Edelman, E., et al. "Pathobiologic Responses to Stenting", American Journal of Cardiology vol. 91, Issue 7, Suppl. 1 (Apr. 1998) pp. 4E-6E.

Farb, A. et al., "Vascular Smooth Muscle Cell Cytotoxicity and Sustained Inhibition of Neointimal Formation by Fibroblast Growth Factor 2-Saporin Fusion Protein", Circ. Res. vol. 80, No. 4, pp. 542-550 (1997).

Ferns, G.A. et al., "Inhibition of Neointimal Smooth Muscle Accumulation After Angioplasty by an Antibody to PDGF", Science, vol. 253, pp. 1129-1132 (1991).

Fischman, D., et al. "A Randomized Comparison of Coronary-Stent Placement and Balloon Angioplasty in the Treatment of Coronary Artery Disease", The New England Journal of Medicine, vol. 331:496-501 (1994).

Franklin and Faxon S., et al. "Pharmacologic Prevention of Restenosis After Coronary Angioplasty: Review of the Randomized Clinical Trials", Coronary Artery Disease, vol. 4, No. 3 (Mar. 1993).

Fukuyama J., et al., "Tranilast Suppresses the Vascular Intimal Hyperplasia After Balloon Injury in Rabbits Fed on a High-Cholesterol Diet", European Journal of Pharmacology 318, pp. 327-332 (1996).

Guyton, J.R. et al., "Inhibition of Rat Arterial Smooth Muscle Cell Proliferation by Heparin", Circulation Research, vol. 46, No. 5, pp. 625-634 (1980).

Hanson, S.R. et al., "Interruption of Acute Platelet-Dependent Thrombosis by the Synthetic Antithrombin D-Phenylalanyl-L-Prolyl-L-Arginyl Chloromethyl Ketone"; Roc. Natl. Acad. Sci. USA (May 1988) 85: 3184-3188.

Hansson, G.K., et al., "Interferon-$\gamma$ Inhibits Arterial Stenosis After Injury" Circulation, vol. 84, No. 3, pp. 1266-1272 (1991).

Jonasson, L. et al., "Cyclosporin A Inhibits Smooth Muscle Proliferation in the Vascular Response to Injury", Proc. Natl. Acad. Sci. USA vol. 85, pp. 2303-2306, (1988).

Lang R., et al. "Effects of Okadaic Acid and ATP$\gamma$S on Cell Length and $CA^{2+}$—Channel Currents Recorded in single Smooth Muscle Cells of the Guinea-Pig Taenia Caeci", Br. J. Pharmacol. 104, p. 331-336 (1991).

Liu, M.W. et al., "Trapidil in Preventing Restenosis After Balloon Angioplasty in the Atherosclerotic Rabbit", Circ. vol. 81, No. 3, pp. 1089-1093 (1990).

Lundergan, C.F. et al., "Peptide Inhibition of Myointimal Proliferation by Angiopeptin, a Somatostatin Analogue", JACC vol. 17(Supp. B), No. 6. pp. 132B-136B (1991).

Majesky, M.W. et al., "Heparin Regulates Smooth Muscle S Phase Entry in the Injured Rat Carotid Artery", Circ. Res. vol. 61, No. 2, pp. 296-300 (1987).

Mak and Topol, "Clinical Trials to Prevent Restenosis after Percutaneous Coronary Revascularization", Department of Cardiolog, Cleveland Clinical Foundation, Ohio p. 255 (1991).

Marx, S.O., et al., "Rapamycin-FKBP Inhibits Cell Cycle Regulators of Proliferation in Vascular Smooth Muscle Cells", Circ. Res., vol. 76, No. 3, pp. 412-417 (1995).

Nemecek, G.M. et al., "Terbinafine Inhibits the Mitogenic Response to Platelet-Derived Growth Factor in Vitro and Neointimal Proliferation in Vivo", J. Pharmacol. Exp. Thera. vol. 248, No. 3, pp. 1167-1174 (1989).

Okada, T. et al., Localized Release of Perivascular Heparin Inhibits Intimal Proliferation after Endothelial Injury without Systemic Anticoagulation, Neurosurgery, vol. 25, No. 6, pp. 892-898 (1989).

Pompa, J., et al. "Clinical Trials of Restenosis After Coronary Angioplasty", American Heart Association, Circulation, (1991) 84:1426-1436.

Powell, J.S. et al., Inhibitors of Antiotensin-Converting Enzyme Prevent Myointimal Proliferation After Vascular Injury, Science, vol. 245, pp. 186-188 (1989).

Serruys P., et al. "Evaluation of Ketanserin in the Prevention of Restenosis After Percutaneous Transluminal Coronary Angioplasty. A Multicenter Randomized Double-Blind Placebo-Controlled Trial", American Heart Association, Circulation, 88, p. 1588 (1993).

Serruys, P., et al. "A Comparison of Balloon-Expandable-Stent Implantation with Balloon Angioplasty in Patients with Coronary Artery Disease", New England Journal of Medicine, vol. 331:489-495 (1994).

Serruys, P., et al. "Heparin-Coated Palmaz-Schatz Stents in Human Coronary Arteries: Early Outcome of the Benestent-II Pilot Study", Circulation of the American Heart Association, vol. 93(3) p. 412-422 (1996).

Simons, M. et al., "Antisense c-*myb* oligonucleotides inhibit intimal arterial smooth muscle cell accumulation in vivo", Nature, vol. 359, pp. 67-70 (1992).

Snow, A.D. et al., "Heparin Modulates the Composition of the Extracellular Matrix Domain Surrounding Arterial Smooth Muscle Cells", vol. 137, No. 2, pp. 313-330, (1990).

Sollot, S.J. et al., "Taxol Inhibits Neointimal Smooth Muscle Cell Accumulation after Angioplasty in the Rat", J. Clinical Investigation, Inc. vol. 95, pp. 1869-1876, (1995).

Tanaka, H., et al. "Sustained Activation of Vascular Cells and Leukocytes in the Rabbit Aorta After Balloon Injury", Circulation, vol. 88, 1788-1803 (1993).

Tardif, J-C., et al. "Probucol and Multivitamins in the Prevention of Restenosis After Coronary Angioplasty", New England Journal of Medicine, vol. 337:365-372 (1997).

Teirstein, P., et al. "Catheter-Based Radiotherapy to Inhibit Restenosis After Coronary Stenting", The New England Journal of Medicine, vol. 336 p. 1697 (Jun. 1997).

Weinberger, J. et al., "Intracoronary Irradiation: Dose Response for the Prevention of Restenosis in Swine", Int. J. Radiation Onc. Biol. Phys. vol. 36, No. 4, pp. 767-775 (1996).

Wiley and Sons, "Fluoro Carbon Elastomers, Modern Fluoropolymers", Wiley Series in Polymer Science, p. 71-90 (1997).

Yokoi H., et al. "Effectiveness of an Antioxidant in Preventing Restenosis After Percutaneous Transluminal Coronary Angioplasty: The Probucol Angioplasty Restenosis Trial", JACC vol. 30, No. 4 p. 855-862 (1997).

Hidalgo, M., et al. "The Rapamycin-Sensitive Signal Transduction Pathway as a Target for Cancer Therapy", Onogene (2000) vol. 19,p. 6680-6686.

Luengo, J., et al. "Structure-Activity Studies of Rapamycin Analogs: Evidence that the C-7 Methoxy Group is Part of the Effector Domain and Positioned at the FKBP12-FRAP Interface", Chemistry & Biology (1995) vol. 2,pp. 471-481.

Tournut, C., et al. "Thermoplastic Copolymers of Vinylidene Fluoride", Modern Fluoropolymers (1997), Chapter 31, pp. 577-596.

Zaragoza, D., et al. "Rapamycin Induces the $G_0$ Program of Transcriptional Repression in Yeast by Interfering with the TOR Signaling Pathway", Molecular and Cellular Biology (1998) vol. 18, No. 8, pp. 4463-4470.

Examiner's Decision of Refusal dated Jan. 5, 2010 for Japanese Patent Application No. 2003-124185.

Notification of Reasons for Refusal dated Apr. 21, 2009 for Japanese Patent Application No. 2003-124185 (WO 01/87375 was previously cited).

European Search Report dated Oct. 21, 2004 for Application No. EP03258243.

U.S. Appl. No. 07/819,314, filed Jan. 9, 1992, Morris.

U.S. Appl. No. 08/424,884, filed Apr. 19, 1995, Helmus et al.

U.S. Appl. No. 08/526,273, filed Sep. 11, 1995, Ding.

U.S. Appl. No. 08/730,542, filed Oct. 11, 1996, Helmus.
U.S. Appl. No. 09/575,480, filed May 19, 2000, Kopia
U.S. Appl. No. 09/001,102, filed Dec. 30, 1997, Khuoli.
U.S. Appl. No. 10/431,059, filed May 7, 2003, Falotico
U.S. Appl. No. 11/454,407, filed Jun. 2006, Llanos et al.
U.S. Appl. No. 11/735,773, filed Apr. 16, 2007, Llanos et al.
U.S. Appl. No. 11/736,271, filed Apr. 17, 2007, Llanos et al.
U.S. Appl. No. 11/736,043, filed Apr. 17, 2007, Llanos et al.
U.S. Appl. No. 11/736137, filed Apr. 17, 2007, Llanos et al.
U.S. Appl. No. 11/941,233, filed Nov. 16, 2007, Llanos et al.
U.S. Appl. No. 11/941,351, filed Nov. 16, 2007, Llanos et al.
U.S. Appl. No. 11/941,449, filed Nov. 16, 2007, Llanos et al.
U.S. Appl. No. 11/941,596, filed Nov. 16, 2007, Llanos et al.
U.S. Appl. No. 90/008,372, filed Mar. 9, 2007, Llanos et al.
U.S. Appl. No. 95/001,095, filed Oct. 24, 2008, Falotico et al.
U.S. Appl. No. 95/001,096, filed Oct. 24, 2008, Falotico et al.
U.S. Appl. No. PCT/US01/30431, filed Sep. 28, 2001, Lentz.
US 5,795,772, 08/1998, Bianco et al. (withdrawn)

* cited by examiner

COATED MEDICAL DEVICES

CROSS REFERENCE TO RELATED APPLICATIONS

This application is a continuation-in-part application of U.S. application Ser. No. 09/887,464 filed Jun. 22, 2001, now U.S. Pat. No. 7,261,735 a continuation-in-part application of U.S. application Ser. No. 09/675,882, filed Sep. 29, 2000, now abandoned and a continuation-in-part of U.S. application Ser. No. 09/850,482 filed May 7, 2001 now abandoned.

BACKGROUND OF THE INVENTION

1. Field of the Invention

The present invention relates to the local administration of drug/drug combinations for the prevention and treatment of vascular disease, and more particularly to intraluminal medical devices for the local delivery of drug/drug combinations for the prevention and treatment of vascular disease caused by injury and methods for maintaining the drug/drug combinations on the intraluminal medical devices. The present invention also relates to medical devices having drugs, agents or compounds affixed thereto to minimize or substantially eliminate a biological organism's reaction to the introduction of the medical device to the organism.

2. Discussion of the Related Art

Many individuals suffer from circulatory disease caused by a progressive blockage of the blood vessels that profuse the heart and other major organs with nutrients. More severe blockage of blood vessels in such individuals often leads to hypertension, ischemic injury, stroke, or myocardial infarction. Atherosclerotic lesions, which limit or obstruct coronary blood flow, are the major cause of ischemic heart disease. Percutaneous transluminal coronary angioplasty is a medical procedure whose purpose is to increase blood flow through an artery. Percutaneous transluminal coronary angioplasty is the predominant treatment for coronary vessel stenosis. The increasing use of this procedure is attributable to its relatively high success rate and its minimal invasiveness compared with coronary bypass surgery. A limitation associated with percutaneous transluminal coronary angioplasty is the abrupt closure of the vessel which may occur immediately after the procedure and restenosis which occurs gradually following the procedure. Additionally, restenosis is a chronic problem in patients who have undergone saphenous vein bypass grafting. The mechanism of acute occlusion appears to involve several factors and may result from vascular recoil with resultant closure of the artery and/or deposition of blood platelets and fibrin along the damaged length of the newly opened blood vessel.

Restenosis after percutaneous transluminal coronary angioplasty is a more gradual process initiated by vascular injury. Multiple processes, including thrombosis, inflammation, growth factor and cytokine release, cell proliferation, cell migration and extracellular matrix synthesis each contribute to the restenotic process.

While the exact mechanism of restenosis is not completely understood, the general aspects of the restenosis process have been identified. In the normal arterial wall, smooth muscle cells proliferate at a low rate, approximately less than 0.1 percent per day. Smooth muscle cells in the vessel walls exist in a contractile phenotype characterized by eighty to ninety percent of the cell cytoplasmic volume occupied with the contractile apparatus. Endoplasmic reticulum, Golgi, and free ribosomes are few and are located in the perinuclear region. Extracellular matrix surrounds the smooth muscle cells and is rich in heparin-like glycosylaminoglycans which are believed to be responsible for maintaining smooth muscle cells in the contractile phenotypic state (Campbell and Campbell, 1985).

Upon pressure expansion of an intracoronary balloon catheter during angioplasty, smooth muscle cells within the vessel wall become injured, initiating a thrombotic and inflammatory response. Cell derived growth factors such as platelet derived growth factor, basic fibroblast growth factor, epidermal growth factor, thrombin, etc., released from platelets, invading macrophages and/or leukocytes, or directly from the smooth muscle cells provoke a proliferative and migratory response in medial smooth muscle cells. These cells undergo a change from the contractile phenotype to a synthetic phenotype characterized by only a few contractile filament bundles, extensive rough endoplasmic reticulum, Golgi and free ribosomes. Proliferation/migration usually begins within one to two days post-injury and peaks several days thereafter (Campbell and Campbell, 1987; Clowes and Schwartz, 1985).

Daughter cells migrate to the intimal layer of arterial smooth muscle and continue to proliferate and secrete significant amounts of extracellular matrix proteins. Proliferation, migration and extracellular matrix synthesis continue until the damaged endothelial layer is repaired at which time proliferation slows within the intima, usually within seven to fourteen days post-injury. The newly formed tissue is called neointima. The further vascular narrowing that occurs over the next three to six months is due primarily to negative or constrictive remodeling.

Simultaneous with local proliferation and migration, inflammatory cells adhere to the site of vascular injury. Within three to seven days post-injury, inflammatory cells have migrated to the deeper layers of the vessel wall. In animal models employing either balloon injury or stent implantation, inflammatory cells may persist at the site of vascular injury for at least thirty days (Tanaka et al., 1993; Edelman et al., 1998). Inflammatory cells therefore are present and may contribute to both the acute and chronic phases of restenosis.

Numerous agents have been examined for presumed antiproliferative actions in restenosis and have shown some activity in experimental animal models. Some of the agents which have been shown to successfully reduce the extent of intimal hyperplasia in animal models include: heparin and heparin fragments (Clowes, A. W. and Karnovsky M., Nature 265: 25-26, 1977; Guyton, J. R. et al., Circ. Res., 46: 625-634, 1980; Clowes, A. W. and Clowes, M. M., Lab. Invest. 52: 611-616, 1985; Clowes, A. W. and Clowes, M. M., Circ. Res. 58: 839-845, 1986; Majesky et al., Circ. Res. 61: 296-300, 1987; Snow et al., Am. J. Pathol. 137: 313-330, 1990; Okada, T. et al., Neurosurgery 25: 92-98, 1989), colchicine (Currier, J. W. et al., Circ. 80: 11-66, 1989), taxol (Sollot, S. J. et al., J. Clin. Invest. 95: 1869-1876, 1995), angiotensin converting enzyme (ACE) inhibitors (Powell, J. S. et al., Science, 245: 186-188, 1989), angiopeptin (Lundergan, C. F. et al. Am. J. Cardiol. 17(Suppl. B):132B-136B, 1991), cyclosporin A (Jonasson, L. et al., Proc. Natl., Acad. Sci., 85: 2303, 1988), goat-anti-rabbit PDGF antibody (Ferns, G. A. A., et al., Science 253: 1129-1132, 1991), terbinafine (Nemecek, G. M. et al., J. Pharmacol. Exp. Thera. 248: 1167-1174, 1989), trapidil (Liu, M. W. et al., Circ. 81: 1089-1093, 1990), tranilast (Fukuyama, J. et al., Eur. J. Pharmacol. 318: 327-332, 1996), interferon-gamma (Hansson, G. K. and Holm, J., Circ. 84: 1266-1272, 1991), rapamycin (Marx, S. O. et al., Circ. Res. 76: 412-417, 1995), steroids (Colburn, M. D. et al., J. Vasc. Surg. 15: 510-518, 1992), see also Berk, B. C. et al., J. Am. Coll.

Cardiol. 17: 111B-117B, 1991), ionizing radiation (Weinberger, J. et al., Int. J. Rad. Onc. Biol. Phys. 36: 767-775, 1996), fusion toxins (Farb, A. et al., Circ. Res. 80: 542-550, 1997) antisense oligionucleotides (Simons, M. et al., Nature 359: 67-70, 1992) and gene vectors (Chang, M. W. et al., J. Clin. Invest. 96: 2260-2268, 1995). Anti-proliferative action on smooth muscle cells in vitro has been demonstrated for many of these agents, including heparin and heparin conjugates, taxol, tranilast, colchicine, ACE inhibitors, fusion toxins, antisense oligionucleotides, rapamycin and ionizing radiation. Thus, agents with diverse mechanisms of smooth muscle cell inhibition may have therapeutic utility in reducing intimal hyperplasia.

However, in contrast to animal models, attempts in human angioplasty patients to prevent restenosis by systemic pharmacologic means have thus far been unsuccessful. Neither aspirin-dipyridamole, ticlopidine, anti-coagulant therapy (acute heparin, chronic warfarin, hirudin or hirulog), thromboxane receptor antagonism nor steroids have been effective in preventing restenosis, although platelet inhibitors have been effective in preventing acute reocclusion after angioplasty (Mak and Topol, 1997; Lang et al., 1991; Popma et al., 1991). The platelet GP $II_b/III_a$ receptor, antagonist, Reopro® is still under study but Reopro® has not shown definitive results for the reduction in restenosis following angioplasty and stenting. Other agents, which have also been unsuccessful in the prevention of restenosis, include the calcium channel antagonists, prostacyclin mimetics, angiotensin converting enzyme inhibitors, serotonin receptor antagonists, and anti-proliferative agents. These agents must be given systemically, however, and attainment of a therapeutically effective dose may not be possible; anti-proliferative (or anti-restenosis) concentrations may exceed the known toxic concentrations of these agents so that levels sufficient to produce smooth muscle inhibition may not be reached (Mak and Topol, 1997; Lang et al., 1991; Popma et al., 1991).

Additional clinical trials in which the effectiveness for preventing restenosis utilizing dietary fish oil supplements or cholesterol lowering agents has been examined showing either conflicting or negative results so that no pharmacological agents are as yet clinically available to prevent post-angioplasty restenosis (Mak and Topol, 1997; Franklin and Faxon, 1993: Serruys, P. W. et al., 1993). Recent observations suggest that the antilipid/antioxidant agent, probucol, may be useful in preventing restenosis but this work requires confirmation (Tardif et al., 1997; Yokoi, et al., 1997). Probucol is presently not approved for use in the United States and a thirty-day pretreatment period would preclude its use in emergency angioplasty. Additionally, the application of ionizing radiation has shown significant promise in reducing or preventing restenosis after angioplasty in patients with stents (Teirstein et al., 1997). Currently, however, the most effective treatments for restenosis are repeat angioplasty, atherectomy or coronary artery bypass grafting, because no therapeutic agents currently have Food and Drug Administration approval for use for the prevention of post-angioplasty restenosis.

Unlike systemic pharmacologic therapy, stents have proven useful in significantly reducing restenosis. Typically, stents are balloon-expandable slotted metal tubes (usually, but not limited to, stainless steel), which, when expanded within the lumen of an angioplastied coronary artery, provide structural support through rigid scaffolding to the arterial wall. This support is helpful in maintaining vessel lumen patency. In two randomized clinical trials, stents increased angiographic success after percutaneous transluminal coronary angioplasty, by increasing minimal lumen diameter and reducing, but not eliminating, the incidence of restenosis at six months (Serruys et al., 1994; Fischman et al., 1994).

Additionally, the heparin coating of stents appears to have the added benefit of producing a reduction in sub-acute thrombosis after stent implantation (Serruys et al., 1996). Thus, sustained mechanical expansion of a stenosed coronary artery with a stent has been shown to provide some measure of restenosis prevention, and the coating of stents with heparin has demonstrated both the feasibility and the clinical usefulness of delivering drugs locally, at the site of injured tissue.

As stated above, the use of heparin coated stents demonstrates the feasibility and clinical usefulness of local drug delivery; however, the manner in which the particular drug or drug combination is affixed to the local delivery device will play a role in the efficacy of this type of treatment. For example, the processes and materials utilized to affix the drug/drug combinations to the local delivery device should not interfere with the operations of the drug/drug combinations. In addition, the processes and materials utilized should be biocompatible and maintain the drug/drug combinations on the local device through delivery and over a given period of time. For example, removal of the drug/drug combination during delivery of the local delivery device may potentially cause failure of the device.

Accordingly, there exists a need for drug/drug combinations and associated local delivery devices for the prevention and treatment of vascular injury causing intimal thickening which is either biologically induced, for example, atherosclerosis, or mechanically induced, for example, through percutaneous transluminal coronary angioplasty. In addition, there exists a need for maintaining the drug/drug combinations on the local delivery device through delivery and positioning as well as ensuring that the drug/drug combination is released in therapeutic dosages over a given period of time.

A variety of stent coatings and compositions have been proposed for the prevention and treatment of injury causing intimal thickening. The coatings may be capable themselves of reducing the stimulus the stent provides to the injured lumen wall, thus reducing the tendency towards thrombosis or restenosis. Alternately, the coating may deliver a pharmaceutical/therapeutic agent or drug to the lumen that reduces smooth muscle tissue proliferation or restenosis. The mechanism for delivery of the agent is through diffusion of the agent through either a bulk polymer or through pores that are created in the polymer structure, or by erosion of a biodegradable coating.

Both bioabsorbable and biostable compositions have been reported as coatings for stents. They generally have been polymeric coatings that either encapsulate a pharmaceutical/therapeutic agent or drug, e.g. rapamycin, taxol etc., or bind such an agent to the surface, e.g. heparin-coated stents. These coatings are applied to the stent in a number of ways, including, though not limited to, dip, spray, or spin coating processes.

One class of biostable materials that has been reported as coatings for stents is polyfluoro homopolymers. Polytetrafluoroethylene (PTFE) homopolymers have been used as implants for many years. These homopolymers are not soluble in any solvent at reasonable temperatures and therefore are difficult to coat onto small medical devices while maintaining important features of the devices (e.g. slots in stents).

Stents with coatings made from polyvinylidenefluoride homopolymers and containing pharmaceutical/therapeutic agents or drugs for release have been suggested. However, like most crystalline polyfluoro homopolymers, they are difficult to apply as high quality films onto surfaces without subjecting them to relatively high temperatures, that correspond to the melting temperature of the polymer.

It would be advantageous to develop coatings for implantable medical devices that will reduce thrombosis, restenosis, or other adverse reactions, that may include, but do not require, the use of pharmaceutical or therapeutic agents or drugs to achieve such affects, and that possess physical and mechanical properties effective for use in such devices even when such coated devices are subjected to relatively low maximum temperatures.

SUMMARY OF THE INVENTION

The drug/drug combination therapies, drug/drug combination carriers and associated local delivery devices of the present invention provide a means for overcoming the difficulties associated with the methods and devices currently in use, as briefly described above. In addition, the methods for maintaining the drug/drug combination therapies, drug/drug combination carriers on the local delivery device ensure that the drug/drug combination therapies reach the target site.

In accordance with one aspect, the present invention is directed to a device for joining substantially tubular organs in a living organism. The device comprises an anastomosis device for connecting a graft vessel to a target vessel such that the two vessels are in fluid communication, a biocompatible vehicle affixed to at least a portion of the anastomosis device, and at least one agent in therapeutic dosages incorporated into the biocompatible vehicle for the treatment of reactions by the living organism caused by the anastomosis device or the implantation thereof.

In accordance with another aspect, the present invention is directed to a medical device for joining tissue in a living organism. The device comprises a surgical clip for sealingly connecting a graft vessel to a target vessel, a biocompatible vehicle affixed to at least a portion of the surgical clip, and at least one agent in therapeutic dosages incorporated into the biocompatible vehicle for the treatment of reactions by the living organism caused by the surgical clip or the implantation thereof.

The medical devices, drug coatings and methods for maintaining the drug coatings or vehicles thereon of the present invention utilizes a combination of materials to treat disease, and reactions by living organisms due to the implantation of medical devices for the treatment of disease or other conditions. The local delivery of drugs, agents or compounds generally substantially reduces the potential toxicity of the drugs, agents or compounds when compared to systemic delivery while increasing their efficacy.

Drugs, agents or compounds may be affixed to any number of medical devices to treat various diseases. The drugs, agents or compounds may also be affixed to minimize or substantially eliminate the biological organism's reaction to the introduction of the medical device utilized to treat a separate condition. For example, stents may be introduced to open coronary arteries or other body lumens such as biliary ducts. The introduction of these stents cause a smooth muscle cell proliferation effect as well as inflammation. Accordingly, the stents may be coated with drugs, agents or compounds to combat these reactions. Anastomosis devices, routinely utilized in certain types of surgery, may also cause a smooth muscle cell proliferation effect as well as inflammation. Therefore, the devices may also be coated with drugs, agents and/or compounds to combat these reactions.

The drugs, agents or compounds will vary depending upon the type of medical device, the reaction to the introduction of the medical device and/or the disease sought to be treated. The type of coating or vehicle utilized to immobilize the drugs, agents or compounds to the medical device may also vary depending on a number of factors, including the type of medical device, the type of drug, agent or compound and the rate of release thereof.

In order to be effective, the drugs, agents or compounds should preferably remain on the medical devices during delivery and implantation. Accordingly, various coating techniques for creating strong bonds between the drugs, agents or compounds may be utilized. In addition, various materials may be utilized as surface modifications to prevent the drugs, agents or compounds from coming off prematurely.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Figure 1:
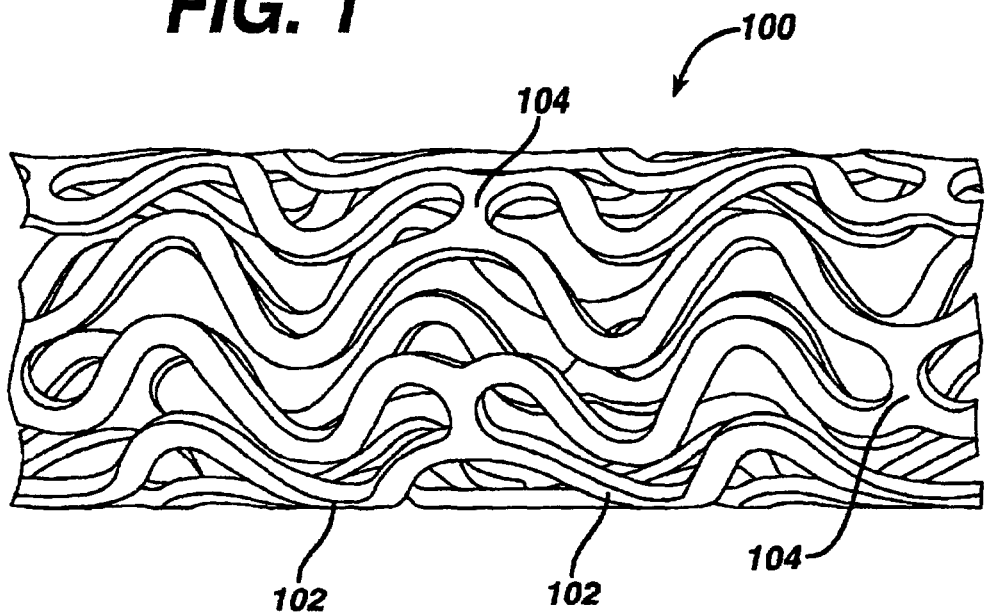
FIG. 1 is a view along the length of a stent (ends not shown) prior to expansion showing the exterior surface of the stent and the characteristic banding pattern.

The drug/drug combinations and delivery devices of the present invention may be utilized to effectively prevent and treat vascular disease, and in particular, vascular disease caused by injury. Various medical treatment devices utilized in the treatment of vascular disease may ultimately induce further complications. For example, balloon angioplasty is a procedure utilized to increase blood flow through an artery and is the predominant treatment for coronary vessel stenosis. However, as stated above, the procedure typically causes a certain degree of damage to the vessel wall, thereby potentially exacerbating the problem at a point later in time. Although other procedures and diseases may cause similar injury, exemplary embodiments of the present invention will be described with respect to the treatment of restenosis and related complications following percutaneous transluminal coronary angioplasty and other similar arterial/venous procedures, including the joining of arteries, veins and other fluid carrying conduits.

While exemplary embodiments of the invention will be described with respect to the treatment of restenosis and related complications following percutaneous transluminal coronary angioplasty, it is important to note that the local delivery of drug/drug combinations may be utilized to treat a wide variety of conditions utilizing any number of medical devices, or to enhance the function and/or life of the device. For example, intraocular lenses, placed to restore vision after cataract surgery is often compromised by the formation of a secondary cataract. The latter is often a result of cellular overgrowth on the lens surface and can be potentially minimized by combining a drug or drugs with the device. Other medical devices which often fail due to tissue in-growth or accumulation of proteinaceous material in, on and around the device, such as shunts for hydrocephalus, dialysis grafts, colostomy bag attachment devices, ear drainage tubes, leads for pace makers and implantable defibrillators can also benefit from the device-drug combination approach. Devices which serve to improve the structure and function of tissue or organ may also show benefits when combined with the appropriate agent or agents. For example, improved osteointegration of orthopedic devices to enhance stabilization of the implanted device could potentially be achieved by combining it with agents such as bone-morphogenic protein. Similarly other surgical devices, sutures, staples, anastomosis devices, vertebral disks, bone pins, suture anchors, hemostatic barriers, clamps, screws, plates, clips, vascular implants, tissue adhesives and sealants, tissue scaffolds, various types of dressings, bone substitutes, intraluminal devices, and vascular supports could also provide enhanced patient benefit using this drug-device combination approach. Essentially, any type of medical device may be coated in some fashion with a drug or drug combination which enhances treatment over use of the singular use of the device or pharmaceutical agent.

In addition to various medical devices, the coatings on these devices may be used to deliver therapeutic and pharmaceutic agents including: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) $II_b/III_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes—dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor signal transduction kinase inhibitors.

As stated previously, the implantation of a coronary stent in conjunction with balloon angioplasty is highly effective in treating acute vessel closure and may reduce the risk of restenosis. Intravascular ultrasound studies (Mintz et al., 1996) suggest that coronary stenting effectively prevents vessel constriction and that most of the late luminal loss after stent implantation is due to plaque growth, probably related to neointimal hyperplasia. The late luminal loss after coronary stenting is almost two times higher than that observed after conventional balloon angioplasty. Thus, inasmuch as stents prevent at least a portion of the restenosis process, a combination of drugs, agents or compounds which prevents smooth muscle cell proliferation, reduces inflammation and reduces coagulation or prevents smooth muscle cell proliferation by multiple mechanisms, reduces inflammation and reduces coagulation combined with a stent may provide the most efficacious treatment for post-angioplasty restenosis. The systemic use of drugs, agents or compounds in combination with the local delivery of the same or different drug/drug combinations may also provide a beneficial treatment option.

The local delivery of drug/drug combinations from a stent has the following advantages; namely, the prevention of vessel recoil and remodeling through the scaffolding action of the stent and the prevention of multiple components of neointimal hyperplasia or restenosis as well as a reduction in inflammation and thrombosis. This local administration of drugs, agents or compounds to stented coronary arteries may also have additional therapeutic benefit. For example, higher tissue concentrations of the drugs, agents or compounds may be achieved utilizing local delivery, rather than systemic administration. In addition, reduced systemic toxicity may be achieved utilizing local delivery rather than systemic administration while maintaining higher tissue concentrations. Also in utilizing local delivery from a stent rather than systemic administration, a single procedure may suffice with better patient compliance. An additional benefit of combination drug, agent, and/or compound therapy may be to reduce the dose of each of the therapeutic drugs, agents or compounds, thereby limiting their toxicity, while still achieving a reduction in restenosis, inflammation and thrombosis. Local stent-based therapy is therefore a means of improving the therapeutic ratio (efficacy/toxicity) of anti-restenosis, anti-inflammatory, anti-thrombotic drugs, agents or compounds.

There are a multiplicity of different stents that may be utilized following percutaneous transluminal coronary angioplasty. Although any number of stents may be utilized in accordance with the present invention, for simplicity, a limited number of stents will be described in exemplary embodiments of the present invention. The skilled artisan will recognize that any number of stents may be utilized in connection with the present invention. In addition, as stated above, other medical devices may be utilized.

A stent is commonly used as a tubular structure left inside the lumen of a duct to relieve an obstruction. Commonly, stents are inserted into the lumen in a non-expanded form and are then expanded autonomously, or with the aid of a second device in situ. A typical method of expansion occurs through the use of a catheter-mounted angioplasty balloon which is inflated within the stenosed vessel or body passageway in order to shear and disrupt the obstructions associated with the wall components of the vessel and to obtain an enlarged lumen.

FIG. 1 illustrates an exemplary stent 100 which may be utilized in accordance with an exemplary embodiment of the present invention. The expandable cylindrical stent 100 comprises a fenestrated structure for placement in a blood vessel, duct or lumen to hold the vessel, duct or lumen open, more particularly for protecting a segment of artery from restenosis after angioplasty. The stent 100 may be expanded circumferentially and maintained in an expanded configuration, that is circumferentially or radially rigid. The stent 100 is axially flexible and when flexed at a band, the stent 100 avoids any externally protruding component parts.

The stent 100 generally comprises first and second ends with an intermediate section therebetween. The stent 100 has a longitudinal axis and comprises a plurality of longitudinally disposed bands 102, wherein each band 102 defines a generally continuous wave along a line segment parallel to the longitudinal axis. A plurality of circumferentially arranged links 104 maintain the bands 102 in a substantially tubular structure. Essentially, each longitudinally disposed band 102 is connected at a plurality of periodic locations, by a short circumferentially arranged link 104 to an adjacent band 102. The wave associated with each of the bands 102 has approximately the same fundamental spatial frequency in the intermediate section, and the bands 102 are so disposed that the wave associated with them are generally aligned so as to be generally in phase with one another. As illustrated in the figure, each longitudinally arranged band 102 undulates through approximately two cycles before there is a link to an adjacent band 102.

The stent 100 may be fabricated utilizing any number of methods. For example, the stent 100 may be fabricated from a hollow or formed stainless steel tube that may be machined using lasers, electric discharge milling, chemical etching or other means. The stent 100 is inserted into the body and placed at the desired site in an unexpanded form. In one exemplary embodiment, expansion may be effected in a blood vessel by a balloon catheter, where the final diameter of the stent 100 is a function of the diameter of the balloon catheter used.

It should be appreciated that a stent 100 in accordance with the present invention may be embodied in a shape-memory material, including, for example, an appropriate alloy of nickel and titanium or stainless steel. Structures formed from stainless steel may be made self-expanding by configuring the stainless steel in a predetermined manner, for example, by twisting it into a braided configuration. In this embodiment after the stent 100 has been formed it may be compressed so as to occupy a space sufficiently small as to permit its insertion in a blood vessel or other tissue by insertion means, wherein the insertion means include a suitable catheter, or flexible rod. On emerging from the catheter, the stent 100 may be configured to expand into the desired configuration where the expansion is automatic or triggered by a change in pressure, temperature or electrical stimulation.

Figure 2:
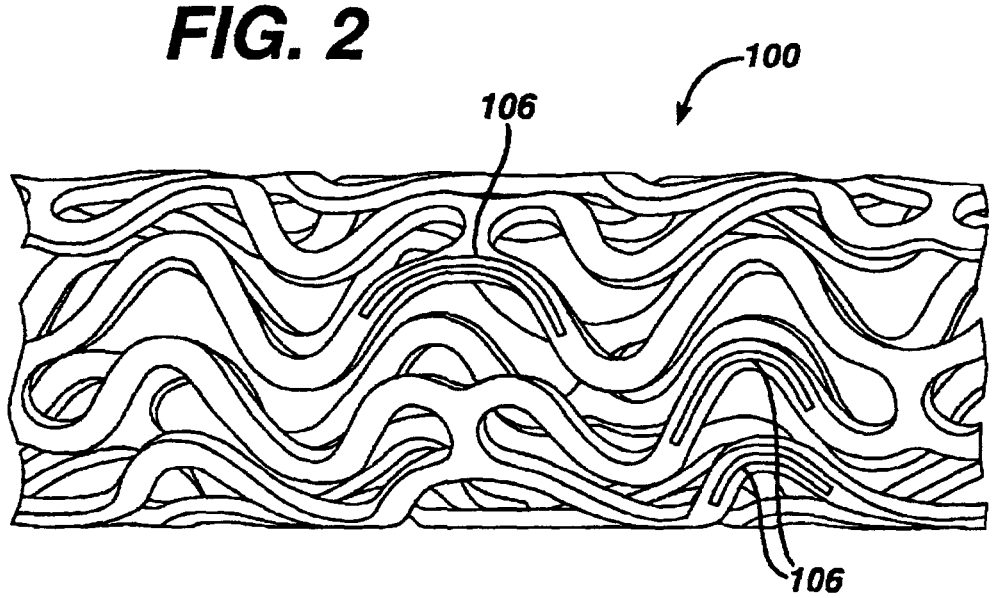
FIG. 2 is a perspective view along the length of the stent of FIG. 1 having reservoirs in accordance with the present invention.

FIG. 2 illustrates an exemplary embodiment of the present invention utilizing the stent 100 illustrated in FIG. 1. As illustrated, the stent 100 may be modified to comprise one or more reservoirs 106. Each of the reservoirs 106 may be opened or closed as desired. These reservoirs 106 may be specifically designed to hold the drug/drug combinations to be delivered. Regardless of the design of the stent 100, it is preferable to have the drug/drug combination dosage applied with enough specificity and a sufficient concentration to provide an effective dosage in the lesion area. In this regard, the reservoir size in the bands 102 is preferably sized to adequately apply the drug/drug combination dosage at the desired location and in the desired amount.

In an alternate exemplary embodiment, the entire inner and outer surface of the stent 100 may be coated with drug/drug combinations in therapeutic dosage amounts. A detailed description of a drug for treating restenosis, as well as exemplary coating techniques, is described below. It is, however, important to note that the coating techniques may vary depending on the drug/drug combinations. Also, the coating techniques may vary depending on the material comprising the stent or other intraluminal medical device.

Rapamycin is a macrocyclic triene antibiotic produced by *Streptomyces hygroscopicus* as disclosed in U.S. Pat. No. 3,929,992. It has been found that rapamycin among other things inhibits the proliferation of vascular smooth muscle cells in vivo. Accordingly, rapamycin may be utilized in treating intimal smooth muscle cell hyperplasia, restenosis, and vascular occlusion in a mammal, particularly following either biologically or mechanically mediated vascular injury, or under conditions that would predispose a mammal to suffering such a vascular injury. Rapamycin functions to inhibit smooth muscle cell proliferation and does not interfere with the re-endothelialization of the vessel walls.

Rapamycin reduces vascular hyperplasia by antagonizing smooth muscle proliferation in response to mitogenic signals that are released during an angioplasty induced injury. Inhibition of growth factor and cytokine mediated smooth muscle proliferation at the late G1 phase of the cell cycle is believed to be the dominant mechanism of action of rapamycin. However, rapamycin is also known to prevent T-cell proliferation and differentiation when administered systemically. This is the basis for its immunosuppresive activity and its ability to prevent graft rejection.

As used herein, rapamycin includes rapamycin and all analogs, derivatives and congeners that find FKBP12, and other immunophilins and possesses the same pharmacologic properties as rapamycin.

Although the anti-proliferative effects of rapamycin may be achieved through systemic use, superior results may be achieved through the local delivery of the compound. Essentially, rapamycin works in the tissues, which are in proximity to the compound, and has diminished effect as the distance from the delivery device increases. In order to take advantage of this effect, one would want the rapamycin in direct contact with the lumen walls. Accordingly, in a preferred embodiment, the rapamycin is incorporated onto the surface of the stent or portions thereof. Essentially, the rapamycin is preferably incorporated into the stent 100, illustrated in FIG. 1, where the stent 100 makes contact with the lumen wall.

Rapamycin may be incorporated onto or affixed to the stent in a number of ways. In the exemplary embodiment, the rapamycin is directly incorporated into a polymeric matrix and sprayed onto the outer surface of the stent. The rapamycin elutes from the polymeric matrix over time and enters the surrounding tissue. The rapamycin preferably remains on the stent for at least three days up to approximately six months, and more preferably between seven and thirty days.

Any number of non-erodible polymers may be utilized in conjunction with the rapamycin. In one exemplary embodiment, the polymeric matrix comprises two layers. The base layer comprises a solution of poly(ethylene-co-vinylacetate) and polybutylmethacrylate. The rapamycin is incorporated into this base layer. The outer layer comprises only polybutylmethacrylate and acts as a diffusion barrier to prevent the rapamycin from eluting too quickly. The thickness of the outer layer or topcoat determines the rate at which the rapamycin elutes from the matrix. Essentially, the rapamycin elutes from the matrix by diffusion through the polymer matrix. Polymers are permeable, thereby allowing solids, liquids and gases to escape therefrom. The total thickness of the polymeric matrix is in the range from about one micron to about twenty microns or greater. It is important to note that primer layers and metal surface treatments may be utilized before the polymeric matrix is affixed to the medical device. For example, acid cleaning, alkaline (base) cleaning, salinization and parylene deposition may be used as part of the overall process described above.

The poly(ethylene-co-vinylacetate), polybutylmethacrylate and rapamycin solution may be incorporated into or onto the stent in a number of ways. For example, the solution may be sprayed onto the stent or the stent may be dipped into the solution. Other methods include spin coating and RF-plasma polymerization. In one exemplary embodiment, the solution is sprayed onto the stent and then allowed to dry. In another exemplary embodiment, the solution may be electrically charged to one polarity and the stent electrically changed to the opposite polarity. In this manner, the solution and stent will be attracted to one another. In using this type of spraying process, waste may be reduced and more precise control over the thickness of the coat may be achieved.

In another exemplary embodiment, the rapamycin or other therapeutic agent may be incorporated into a film-forming polyfluoro copolymer comprising an amount of a first moiety selected from the group consisting of polymerized vinylidenefluoride and polymerized tetrafluoroethylene, and an amount of a second moiety other than the first moiety and which is copolymerized with the first moiety, thereby producing the polyfluoro copolymer, the second moiety being capable of providing toughness or elastomeric properties to the polyfluoro copolymer, wherein the relative amounts of the first moiety and the second moiety are effective to provide the coating and film produced therefrom with properties effective for use in treating implantable medical devices.

The present invention provides polymeric coatings comprising a polyfluoro copolymer and implantable medical devices, for example, stents coated with a film of the polymeric coating in amounts effective to reduce thrombosis and/or restenosis when such stents are used in, for example, angioplasty procedures. As used herein, polyfluoro copolymers means those copolymers comprising an amount of a first moiety selected from the group consisting of polymerized vinylidenefluoride and polymerized tetrafluoroethylene, and an amount of a second moiety other than the first moiety and which is copolymerized with the first moiety to produce the polyfluoro copolymer, the second moiety being capable of providing toughness or elastomeric properties to the polyfluoro copolymer, wherein the relative amounts of the first moiety and the second moiety are effective to provide coatings and film made from such polyfluoro copolymers with properties effective for use in coating implantable medical devices.

The coatings may comprise pharmaceutical or therapeutic agents for reducing restenosis, inflammation, and/or thrombosis, and stents coated with such coatings may provide sustained release of the agents. Films prepared from certain polyfluoro copolymer coatings of the present invention provide the physical and mechanical properties required of conventional coated medical devices, even where maximum temperature, to which the device coatings and films are exposed, are limited to relatively low temperatures. This is particularly important when using the coating/film to deliver pharmaceutical/therapeutic agents or drugs that are heat sensitive, or when applying the coating onto temperature-sensitive devices such as catheters. When maximum exposure temperature is not an issue, for example, where heat-stable agents such as itraconazole are incorporated into the coatings, higher melting thermoplastic polyfluoro copolymers may be used and, if very high elongation and adhesion is required, elastomers may be used. If desired or required, the polyfluoro elastomers may be crosslinked by standard methods described in, e.g., *Modern Fluoropolymers*, (J. Shires ed.), John Wiley & Sons, New York, 1997, pp. 77-87.

The present invention comprises polyfluoro copolymers that provide improved biocompatible coatings or vehicles for medical devices. These coatings provide inert biocompatible surfaces to be in contact with body tissue of a mammal, for example, a human, sufficient to reduce restenosis, or thrombosis, or other undesirable reactions. While many reported coatings made from polyfluoro homopolymers are insoluble and/or require high heat, for example, greater than about one hundred twenty-five degrees centigrade, to obtain films with adequate physical and mechanical properties for use on implantable devices, for example, stents, or are not particularly tough or elastomeric, films prepared from the polyfluoro copolymers of the present invention provide adequate adhesion, toughness or elasticity, and resistance to cracking when formed on medical devices. In certain exemplary embodiments, this is the case even where the devices are subjected to relatively low maximum temperatures.

The polyfluoro copolymers used for coatings according to the present invention are preferably film-forming polymers that have molecular weight high enough so as not to be waxy or tacky. The polymers and films formed therefrom should preferably adhere to the stent and not be readily deformable after deposition on the stent as to be able to be displaced by hemodynamic stresses. The polymer molecular weight should preferably be high enough to provide sufficient toughness so that films comprising the polymers will not be rubbed off during handling or deployment of the stent. In certain exemplary embodiments the coating will not crack where expansion of the stent or other medical devices occurs.

Coatings of the present invention comprise polyfluoro copolymers, as defined hereinabove. The second moiety polymerized with the first moiety to prepare the polyfluoro copolymer may be selected from those polymerized, biocompatible monomers that would provide biocompatible polymers acceptable for implantation in a mammal, while maintaining sufficient elastomeric film properties for use on medical devices claimed herein. Such monomers include, without limitation, hexafluoropropylene (HFP), tetrafluoroethylene (TFE), vinylidenefluoride, 1-hydropentafluoropropylene, perfluoro(methyl vinyl ether), chlorotrifluoroethylene (CTFE), pentafluoropropene, trifluoroethylene, hexafluoroacetone and hexafluoroisobutylene.

Polyfluoro copolymers used in the present invention typically comprise vinylidinefluoride copolymerized with hexafluoropropylene, in the weight ratio in the range of from about fifty to about ninety-two weight percent vinylidinefluoride to about fifty to about eight weight percent HFP. Preferably, polyfluoro copolymers used in the present invention comprise from about fifty to about eighty-five weight percent vinylidinefluoride copolymerized with from about fifty to about fifteen weight percent HFP. More preferably, the polyfluoro copolymers will comprise from about fifty-five to about seventy weight percent vinylidineflyoride copolymerized with from about forty-five to about thirty weight percent HFP. Even more preferably, polyfluoro copolymers comprise from about fifty-five to about sixty-five weight percent vinylidinefluoride copolymerized with from about forty-five to about thirty-five weight percent HFP. Such polyfluoro copolymers are soluble, in varying degrees, in solvents such as dimethylacetamide (DMAc), tetrahydrofuran, dimethyl formamide, dimethyl sulfoxide and n-methyl pyrrolidone. Some are soluble in methylethylketone (MEK), acetone, methanol and other solvents commonly used in applying coatings to conventional implantable medical devices.

Conventional polyfluoro homopolymers are crystalline and difficult to apply as high quality films onto metal surfaces without exposing the coatings to relatively high temperatures that correspond to the melting temperature (Tm) of the polymer. The elevated temperature serves to provide films prepared from such PVDF homopolymer coatings that exhibit sufficient adhesion of the film to the device, while preferably maintaining sufficient flexibility to resist film cracking upon expansion/contraction of the coated medical device. Certain films and coatings according to the present invention provide these same physical and mechanical properties, or essentially the same properties, even when the maximum temperatures to which the coatings and films are exposed is less than about a maximum predetermined temperature. This is particularly important when the coatings/films comprise pharmaceutical or therapeutic agents or drugs that are heat sensitive, for example, subject to chemical or physical degradation or other heat-induced negative affects, or when coating heat sensitive substrates of medical devices, for example, subject to heat-induced compositional or structural degradation.

Depending on the particular device upon which the coatings and films of the present invention are to be applied and the particular use/result required of the device, polyfluoro copolymers used to prepare such devices may be crystalline, semi-crystalline or amorphous.

Where devices have no restrictions or limitations with respect to exposure of same to elevated temperatures, crystalline polyfluoro copolymers may be employed. Crystalline polyfluoro copolymers tend to resist the tendency to flow under applied stress or gravity when exposed to temperatures above their glass transition (Tg) temperatures. Crystalline polyfluoro copolymers provide tougher coatings and films than their fully amorphous counterparts. In addition, crystalline polymers are more lubricious and more easily handled through crimping and transfer processes used to mount self-expanding stents, for example, nitinol stents.

Semi-crystalline and amorphous polyfluoro copolymers are advantageous where exposure to elevated temperatures is an issue, for example, where heat-sensitive pharmaceutical or therapeutic agents are incorporated into the coatings and films, or where device design, structure and/or use preclude exposure to such elevated temperatures. Semi-crystalline polyfluoro copolymer elastomers comprising relatively high levels, for example, from about thirty to about forty-five weight percent of the second moiety, for example, HFP, copolymerized with the first moiety, for example, VDF, have the advantage of reduced coefficient of friction and self-blocking relative to amorphous polyfluoro copolymer elastomers. Such characteristics may be of significant value when processing, packaging and delivering medical devices coated with such polyfluoro copolymers. In addition, such polyfluoro copolymer elastomers comprising such relatively high content of the second moiety serves to control the solubility of certain agents, for example, rapamycin, in the polymer and therefore controls permeability of the agent through the matrix.

Polyfluoro copolymers utilized in the present inventions may be prepared by various known polymerization methods. For example, high pressure, free-radical, semi-continuous emulsion polymerization techniques such as those disclosed in *Fluoroelastomers-dependence of relaxation phenomena on compositions*, POLYMER 30, 2180, 1989, by Ajroldi, et al., may be employed to prepare amorphous polyfluoro copolymers, some of which may be elastomers. In addition, free-radical batch emulsion polymerization techniques disclosed herein may be used to obtain polymers that are semi-crystalline, even where relatively high levels of the second moiety are included.

As described above, stents may comprise a wide variety of materials and a wide variety of geometries. Stents may be made of biocompatible materials, including biostable and bioabsorbable materials. Suitable biocompatible metals include, but are not limited to, stainless steel, tantalum, titanium alloys (including nitinol), and cobalt alloys (including cobalt-chromium nickel alloys). Suitable nonmetallic biocompatible materials include, but are not limited to, polyamides, polyolefins (i.e. polypropylene, polyethylene etc.), nonabsorbable polyesters (i.e. polyethylene terephthalate), and bioabsorbable aliphatic polyesters (i.e. homopolymers and copolymers of lactic acid, glycolic acid, lactide, glycolide, para-dioxanone, trimethylene carbonate, ε-caprolactone, and blends thereof.

The film-forming biocompatible polymer coatings generally are applied to the stent in order to reduce local turbulence in blood flow through the stent, as well as adverse tissue reactions. The coatings and films formed therefrom also may be used to administer a pharmaceutically active material to the site of the stent placement. Generally, the amount of polymer coating to be applied to the stent will vary depending on, among other possible parameters, the particular polyfluoro copolymer used to prepare the coating, the stent design and the desired effect of the coating. Generally, the coated stent will comprise from about 0.1 to about fifteen weight percent of the coating, preferably from about 0.4 to about ten weight percent. The polyfluoro copolymer coatings may be applied in one or more coating steps, depending on the amount of polyfluoro copolymer to be applied. Different polyfluoro copolymers may be used for different layers in the stent coating. In fact, in certain exemplary embodiments, it is highly advantageous to use a diluted first coating solution comprising a polyfluoro copolymer as a primer to promote adhesion of a subsequent polyfluoro copolymer coating layer that may include pharmaceutically active materials. The individual coatings may be prepared from different polyfluoro copolymers.

Additionally, a top coating may be applied to delay release of the pharmaceutical agent, or they could be used as the matrix for the delivery of a different pharmaceutically active material. Layering of coatings may be used to stage release of the drug or to control release of different agents placed in different layers.

Blends of polyfluoro copolymers may also be used to control the release rate of different agents or to provide a desirable balance of coating properties, i.e. elasticity, toughness, etc., and drug delivery characteristics, for example, release profile. Polyfluoro copolymers with different solubilities in solvents may be used to build up different polymer layers that may be used to deliver different drugs or to control the release profile of a drug. For example, polyfluoro copolymers comprising 85.5/14.5 (wt/wt) of poly(vinylidinefluoride/HFP) and 60.6/39.4 (wt/wt) of poly(vinylidinefluoride/HFP) are both soluble in DMAc. However, only the 60.6/39.4 PVDF polyfluoro copolymer is soluble in methanol. So, a first layer of the 85.5/14.5 PVDF polyfluoro copolymer comprising a drug could be over coated with a topcoat of the 60.6/39.4 PVDF polyfluoro copolymer made with the methanol solvent. The top coating may be used to delay the drug delivery of the drug contained in the first layer. Alternately, the second layer could comprise a different drug to provide for sequential drug delivery. Multiple layers of different drugs could be provided by alternating layers of first one polyfluoro copolymer, then the other. As will be readily appreciated by those skilled in the art, numerous layering approaches may be used to provide the desired drug delivery.

Coatings may be formulated by mixing one or more therapeutic agents with the coating polyfluoro copolymers in a coating mixture. The therapeutic agent may be present as a liquid, a finely divided solid, or any other appropriate physical form. Optionally, the coating mixture may include one or more additives, for example, nontoxic auxiliary substances such as diluents, carriers, excipients, stabilizers or the like. Other suitable additives may be formulated with the polymer and pharmaceutically active agent or compound. For example, a hydrophilic polymer may be added to a biocompatible hydrophobic coating to modify the release profile, or a hydrophobic polymer may be added to a hydrophilic coating to modify the release profile. One example would be adding a hydrophilic polymer selected from the group consisting of polyethylene oxide, polyvinyl pyrrolidone, polyethylene glycol, carboxylmethyl cellulose, and hydroxymethyl cellulose to a polyfluoro copolymer coating to modify the release profile. Appropriate relative amounts may be determined by monitoring the in vitro and/or in vivo release profiles for the therapeutic agents.

The best conditions for the coating application are when the polyfluoro copolymer and pharmaceutic agent have a common solvent. This provides a wet coating that is a true solution. Less desirable, yet still usable, are coatings that contain the pharmaceutical agent as a solid dispersion in a solution of the polymer in solvent. Under the dispersion conditions, care must be taken to ensure that the particle size of the dispersed pharmaceutical powder, both the primary powder size and its aggregates and agglomerates, is small enough not to cause an irregular coating surface or to clog the slots of the stent that need to remain essentially free of coating. In cases where a dispersion is applied to the stent and the smoothness of the coating film surface requires improvement, or to be ensured that all particles of the drug are fully encapsulated in the polymer, or in cases where the release rate of the drug is to be slowed, a clear (polyfluoro copolymer only) topcoat of the same polyfluoro copolymer used to provide sustained release of the drug or another polyfluoro copolymer that further restricts the diffusion of the drug out of the coating may be applied. The topcoat may be applied by dip coating with mandrel to clear the slots. This method is disclosed in U.S. Pat. No. 6,153,252. Other methods for applying the topcoat include spin coating and spray coating. Dip coating of the topcoat can be problematic if the drug is very soluble in the coating solvent, which swells the polyfluoro copolymer, and the clear coating solution acts as a zero concentration sink and redissolves previously deposited drug. The time spent in the dip bath may need to be limited so that the drug is not extracted out into the drug-free bath. Drying should be rapid so that the previously deposited drug does not completely diffuse into the topcoat.

The amount of therapeutic agent will be dependent upon the particular drug employed and medical condition being treated. Typically, the amount of drug represents about 0.001 percent to about seventy percent, more typically about 0.001 percent to about sixty percent.

The quantity and type of polyfluoro copolymers employed in the coating film comprising the pharmaceutic agent will vary depending on the release profile desired and the amount of drug employed. The product may contain blends of the same or different polyfluoro copolymers having different molecular weights to provide the desired release profile or consistency to a given formulation.

Polyfluoro copolymers may release dispersed drug by diffusion. This can result in prolonged delivery (over, say approximately one to two-thousand hours, preferably two to eight-hundred hours) of effective amounts (0.001 $\mu g/cm^2$-min to 1000 $\mu g/cm^2$-min) of the drug. The dosage may be tailored to the subject being treated, the severity of the affliction, the judgment of the prescribing physician, and the like.

Individual formulations of drugs and polyfluoro copolymers may be tested in appropriate in vitro and in vivo models to achieve the desired drug release profiles. For example, a drug could be formulated with a polyfluoro copolymer, or blend of polyfluoro copolymers, coated onto a stent and placed in an agitated or circulating fluid system, for example, twenty-five percent ethanol in water. Samples of the circulating fluid could be taken to determine the release profile (such as by HPLC, UV analysis or use of radiotagged molecules). The release of a pharmaceutical compound from a stent coating into the interior wall of a lumen could be modeled in appropriate animal system. The drug release profile could then be monitored by appropriate means such as, by taking samples at specific times and assaying the samples for drug concentration (using HPLC to detect drug concentration). Thrombus formation can be modeled in animal models using the In-platelet imaging methods described by Hanson and Harker, Proc. Natl. Acad. Sci. USA 85:3184-3188 (1988). Following this or similar procedures, those skilled in the art will be able to formulate a variety of stent coating formulations.

While not a requirement of the present invention, the coatings and films may be crosslinked once applied to the medical devices. Crosslinking may be affected by any of the known crosslinking mechanisms, such as chemical, heat or light. In addition, crosslinking initiators and promoters may be used where applicable and appropriate. In those exemplary embodiments utilizing crosslinked films comprising pharmaceutical agents, curing may affect the rate at which the drug diffuses from the coating. Crosslinked polyfluoro copolymers films and coatings of the present invention also may be used without drug to modify the surface of implantable medical devices.

EXAMPLES

Example 1

A PVDF homopolymer (Solef® 1008 from Solvay Advanced Polymers, Houston, Tex., Tm about 175° C.) and polyfluoro copolymers of poly(vinylidenefluoride/HFP), 92/8 and 91/9 weight percent vinylidenefluoride/HFP as determined by $F^{19}$ NMR, respectively (eg: Solef® 11010 and 11008, Solvay Advanced Polymers, Houston, Tex., Tm about 159 degrees C and 160 degrees C, respectively) were examined as potential coatings for stents. These polymers are soluble in solvents such as, but not limited to, DMAc, N,N-dimethylformamide (DMF), dimethyl sulfoxide (DMSO), N-methylpyrrolidone (NMP), tetrahydrofuran (THF) and acetone. Polymer coatings were prepared by dissolving the polymers in acetone, at five weight percent as a primer, or by dissolving the polymer in 50/50 DMAc/acetone, at thirty weight percent as a topcoat. Coatings that were applied to the stents by dipping and dried at 60 degrees C in air for several hours, followed by 60 degrees C for three hours in a <100 mm Hg vacuum, resulted in white foamy films. As applied, these films adhered poorly to the stent and flaked off, indicating they were too brittle. When stents coated in this manner were heated above 175 degrees C, i.e. above the melting temperature of the polymer, a clear, adherent film was formed. Since coatings require high temperatures, for example, above the melting temperature of the polymer, to achieve high quality films. As mentioned above, the high temperature heat treatment is unacceptable for the majority of drug compounds due to their thermal sensitivity.

Example 2

A polyfluoro copolymer (Solef® 21508) comprising 85.5 weight percent vinylidenefluoride copolymerized with 14.5 weight percent HFP, as determined by $F^{19}$ NMR, was evaluated. This copolymer is less crystalline than the polyfluoro homopolymer and copolymers described in Example 1. It also has a lower melting point reported to be about 133 degrees C. Once again, a coating comprising about twenty weight percent of the polyfluoro copolymer was applied from a polymer solution in 50/50 DMAc/MEK. After drying (in air) at 60 degrees C for several hours, followed by 60 degrees C for three hours in a <100 mtorr Hg vacuum, clear adherent films were obtained. This eliminated the need for a high temperature heat treatment to achieve high quality films. Coatings were smoother and more adherent than those of Example 1. Some coated stents that underwent expansion show some degree of adhesion loss and "tenting" as the film pulls away from the metal. Where necessary, modification of coatings containing such copolymers may be made, e.g. by addition of plasticizers or the like to the coating compositions. Films prepared from such coatings may be used to coat stents or other medical devices, particularly where those devices are not susceptible to expansion to the degree of the stents.

The coating process above was repeated, this time with a coating comprising the 85.5/14.6 (wt/wt) (vinylidenefluoride/HFP) and about thirty weight percent of rapamycin (Wyeth-Ayerst Laboratories, Philadelphia, Pa.), based on total weight of coating solids. Clear films that would occasionally crack or peel upon expansion of the coated stents resulted. It is believed that inclusion of plasticizers and the like in the coating composition will result in coatings and films for use on stents and other medical devices that are not susceptible to such cracking and peeling.

Example 3

Polyfluoro copolymers of still higher HFP content were then examined. This series of polymers were not semicrystalline, but rather are marketed as elastomers. One such copolymer is Fluorel™ FC2261Q (from Dyneon, a 3M-Hoechst Enterprise, Oakdale, Minn.), a 60.6/39.4 (wt/wt) copolymer of vinylidenefluoride/HFP. Although this copolymer has a Tg well below room temperature (Tg about minus twenty degrees C) it is not tacky at room temperature or even at sixty degrees C. This polymer has no detectable crystallinity when measured by Differential Scanning Calorimetry (DSC) or by wide angle X-ray diffraction. Films formed on stents as described above were non-tacky, clear, and expanded without incident when the stents were expanded.

The coating process above was repeated, this time with coatings comprising the 60.6/39.4 (wt/wt) (vinylidenefluoride/HFP) and about nine, thirty and fifty weight percent of rapamycin (Wyeth-Ayerst Laboratories, Philadelphia, Pa.), based on total weight of coating solids, respectively. Coatings comprising about nine and thirty weight percent rapamycin provided white, adherent, tough films that expanded without incident on the stent. Inclusion of fifty percent drug, in the same manner, resulted in some loss of adhesion upon expansion.

Changes in the comonomer composition of the polyfluoro copolymer also can affect the nature of the solid state coating, once dried. For example, the semicrystalline copolymer, Solef® 21508, containing 85.5 percent vinylidenefluoride polymerized with 14.5 percent by weight HFP forms homogeneous solutions with about 30 percent rapamycin (drug weight divided by total solids weight, for example, drug plus copolymer) in DMAc and 50/50 DMAc/MEK. When the film is dried (60 degrees C/16 hours followed by 60 degrees C/3 hours in vacuum of 100 mm Hg) a clear coating, indicating a solid solution of the drug in the polymer, is obtained. Conversely, when an amorphous copolymer, Fluorel™ FC2261Q, of PDVF/HFP at 60.6/39.5 (wt/wt) forms a similar thirty percent solution of rapamycin in DMAc/MEK and is similarly dried, a white film, indicating phase separation of the drug and the polymer, is obtained. This second drug containing film is much slower to release the drug into an in vitro test solution of twenty-five percent ethanol in water than is the former clear film of crystalline Solef® 21508. X-ray analysis of both films indicates that the drug is present in a non-crystalline form. Poor or very low solubility of the drug in the high HFP containing copolymer results in slow permeation of the drug through the thin coating film. Permeability is the product of diffusion rate of the diffusing species (in this case the drug) through the film (the copolymer) and the solubility of the drug in the film.

Example 4

In Vitro Release Results of Rapamycin from Coating

Figure 3:
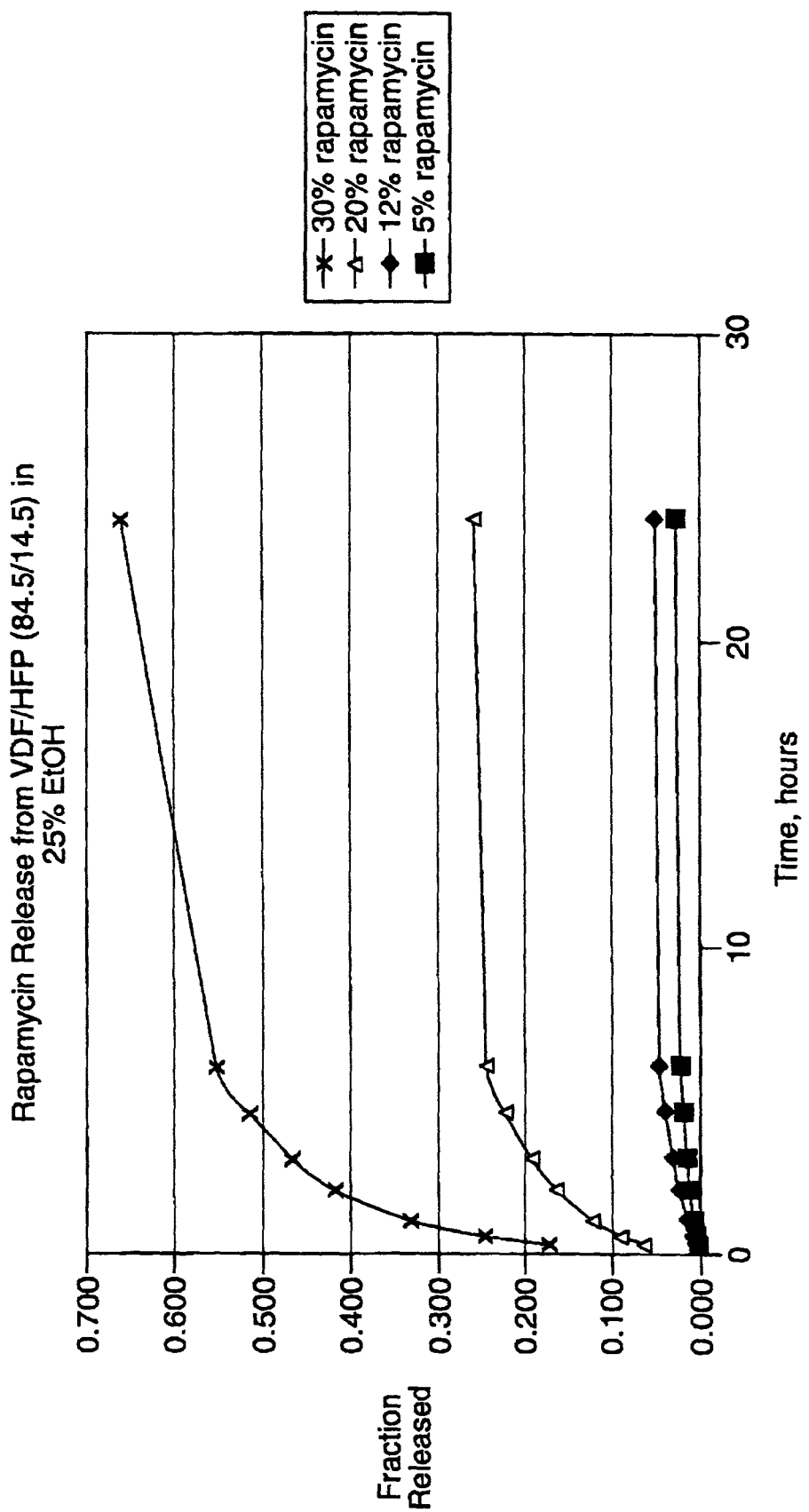
FIG. 3 indicates the fraction of drug released as a function of time from coatings of the present invention over which no topcoat has been disposed.
Figure 4:
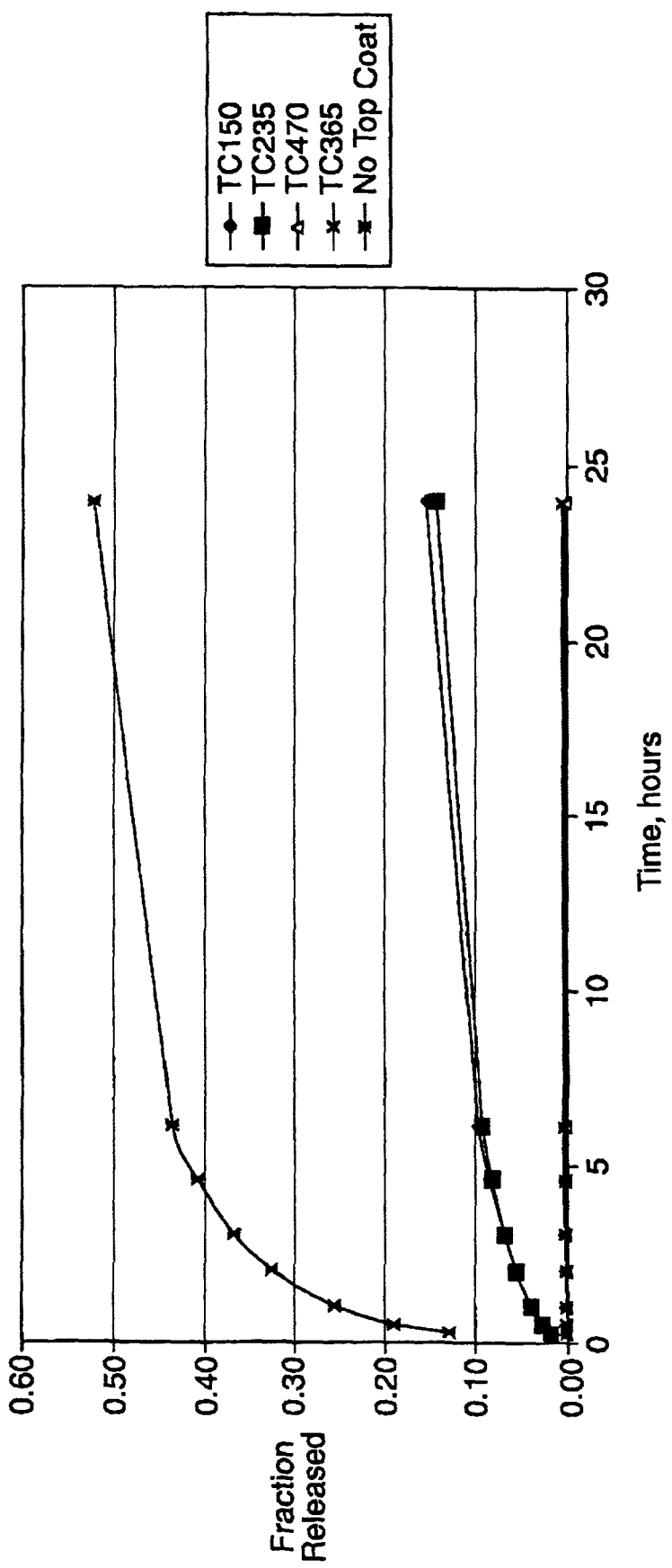
FIG. 4 indicates the fraction of drug released as a function of time from coatings of the present invention including a topcoat disposed thereon.
Figure 5:
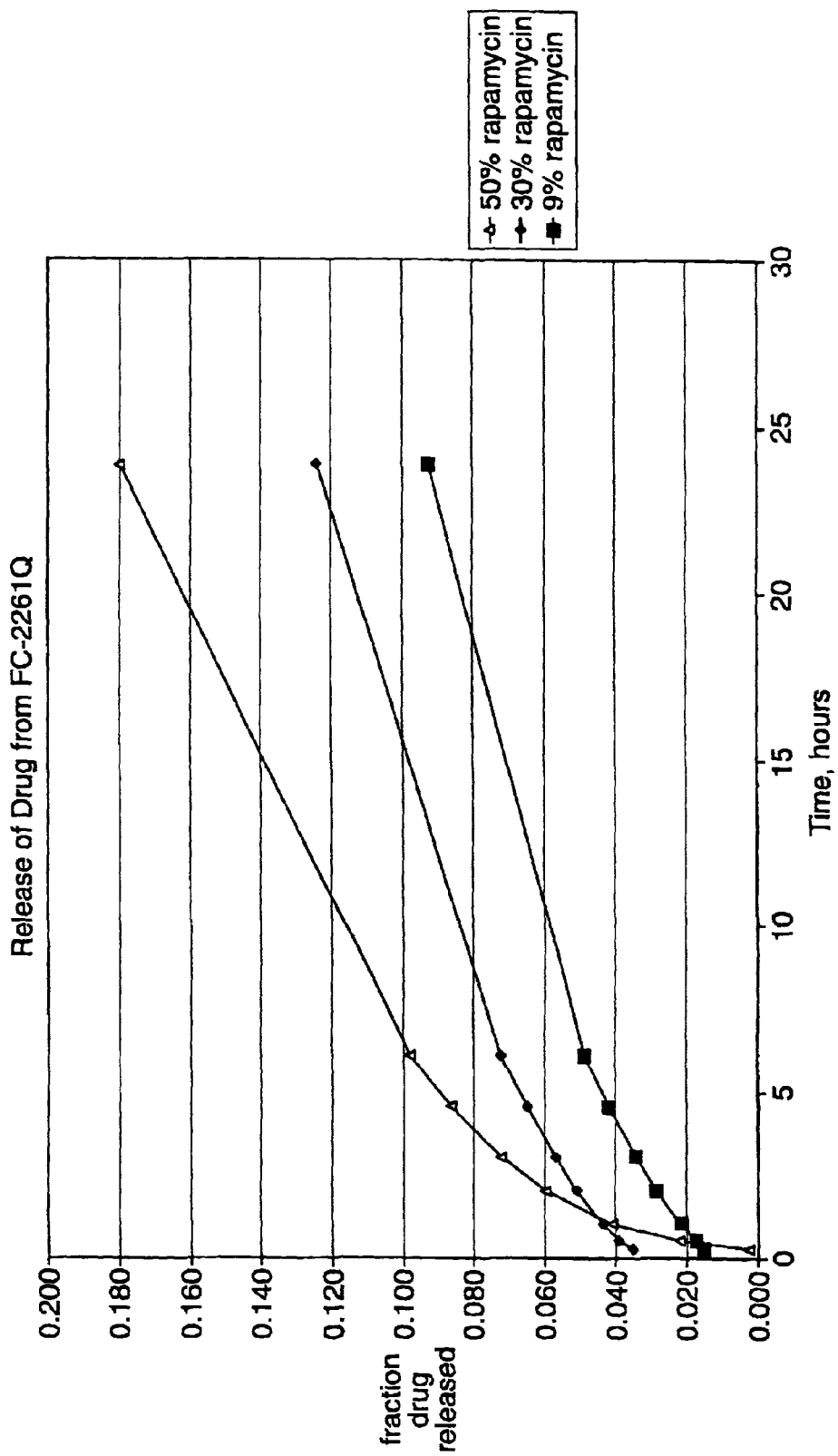
FIG. 5 indicates the fraction of drug released as a function of time from coatings of the present invention over which no topcoat has been disposed.
Figure 6:
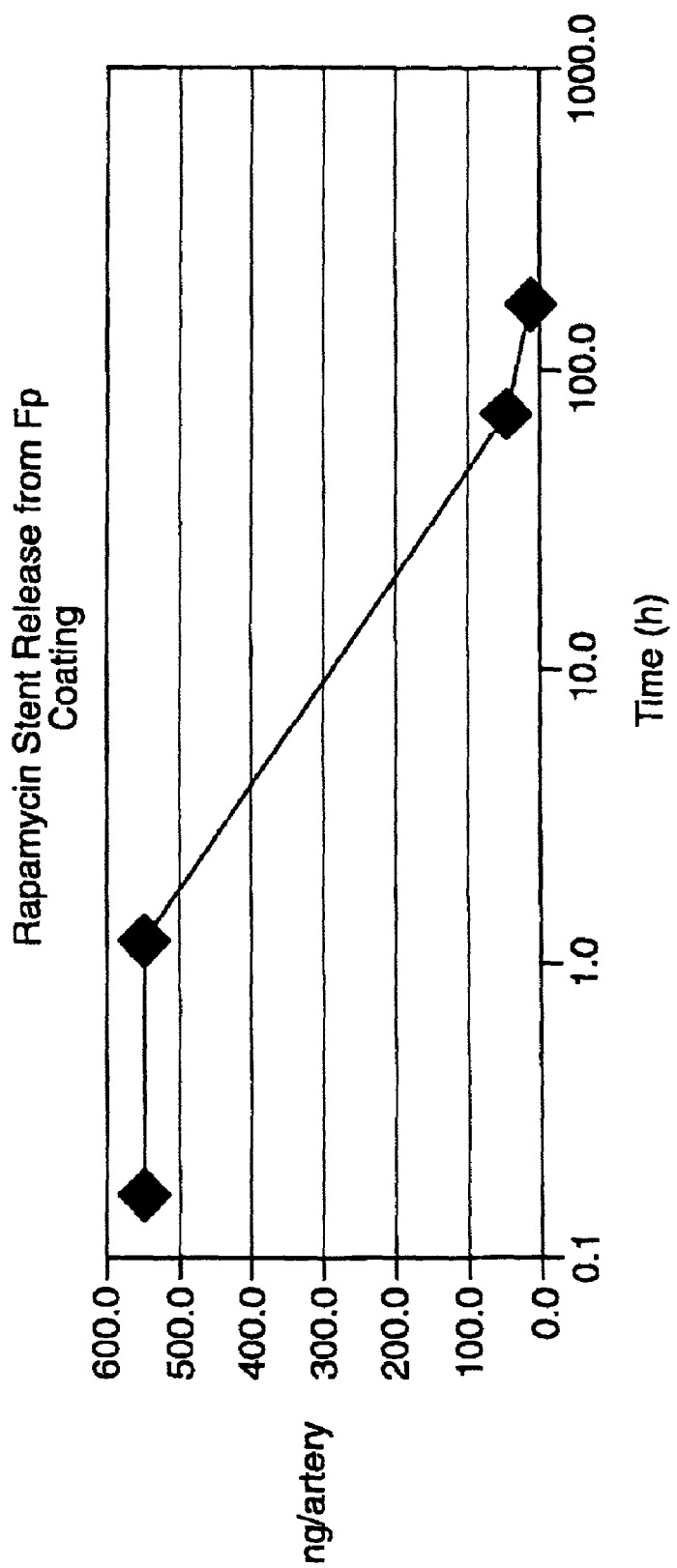
FIG. 6 indicates in vivo stent release kinetics of rapamycin from poly(VDF/HFP).

FIG. 3 is a plot of data for the 85.5/14.5 vinylidenefluoride/HFP polyfluoro copolymer, indicating fraction of drug released as a function of time, with no topcoat. FIG. 4 is a plot of data for the same polyfluoro copolymer over which a topcoat has been disposed, indicating that most effect on release rate is with a clear topcoat. As shown therein, TC150 refers to a device comprising one hundred fifty micrograms of topcoat, TC235 refers to two hundred thirty-five micrograms of topcoat, etc. The stents before topcoating had an average of seven hundred fifty micrograms of coating containing thirty percent rapamycin. FIG. 5 is a plot for the 60.6/39.4 vinylidenefluoride/HFP polyfluoro copolymer, indicating fraction of drug released as a function of time, showing significant control of release rate from the coating without the use of a topcoat. Release is controlled by loading of drug in the film.

Example 5

In Vivo Stent Release Kinetics of Rapamycin from Poly(VDF/HFP)

Nine New Zealand white rabbits (2.5-3.0 kg) on a normal diet were given aspirin twenty-four hours prior to surgery, again just prior to surgery and for the remainder of the study. At the time of surgery, animals were premedicated with Acepromazine (0.1-0.2 mg/kg) and anesthetized with a Ketamine/Xylazine mixture (40 mg/kg and 5 mg/kg, respectively). Animals were given a single intraprocedural dose of heparin (150 IU/kg, i.v.)

Arteriectomy of the right common carotid artery was performed and a 5 F catheter introducer (Cordis, Inc.) placed in the vessel and anchored with ligatures. Iodine contrast agent was injected to visualize the right common carotid artery, brachlocephalic trunk and aortic arch. A steerable guide wire (0.014 inch/180 cm, Cordis, Inc.) was inserted via the introducer and advanced sequentially into each iliac artery to a location where the artery possesses a diameter closest to 2 mm using the angiographic mapping done previously. Two stents coated with a film made of poly(VDF/HFP):(60.6/39.4) with thirty percent rapamycin were deployed in each animal where feasible, one in each iliac artery, using 3.0 mm balloon and inflation to 8-10 ATM for thirty seconds followed after a one minute interval by a second inflation to 8-10 ATM for thirty seconds. Follow-up angiographs visualizing both iliac arteries are obtained to confirm correct deployment position of the stent.

At the end of procedure, the carotid artery was ligated and the skin is closed with 3/0 vicryl suture using a one layered interrupted closure. Animals were given butoropanol (0.4 mg/kg, s.c.) and gentamycin (4 mg/kg, i.m.). Following recovery, the animals were returned to their cages and allowed free access to food and water.

Due to early deaths and surgical difficulties, two animals were not used in this analysis. Stented vessels were removed from the remaining seven animals at the following time points: one vessel (one animal) at ten minutes post implant; six vessels (three animals) between forty minutes and two hours post-implant (average, 1.2 hours); two vessels (two animals) at three days post implant; and two vessels (one animal) at seven days post-implant. In one animal at two hours, the stent was retrieved from the aorta rather than the iliac artery. Upon removal, arteries were carefully trimmed at both the proximal and distal ends of the stent. Vessels were then carefully dissected free of the stent, flushed to remove any residual blood, and both stent and vessel frozen immediately, wrapped separately in foil, labeled and kept frozen at minus eighty degrees C. When all samples had been collected, vessels and stents were frozen, transported and subsequently analyzed for rapamycin in tissue and results are illustrated in FIG. 4.

Example 6

Purifying the Polymer

The Fluorel™ FC2261Q copolymer was dissolved in MEK at about ten weight percent and was washed in a 50/50 mixture of ethanol/water at a 14:1 of ethanol/water to MEK solution ratio. The polymer precipitated out and was separated from the solvent phase by centrifugation. The polymer again was dissolved in MEK and the washing procedure repeated. The polymer was dried after each washing step at sixty degrees C in a vacuum oven (<200 mtorr) over night.

Example 7

In Vivo Testing of Coated Stents in Porcine Coronary Arteries

CrossFlex® stents (available from Cordis, a Johnson & Johnson Company) were coated with the "as received" Fluorel™ FC2261Q PVDF copolymer and with the purified polyfluoro copolymer of Example 6, using the dip and wipe approach. The coated stents were sterilized using ethylene oxide and a standard cycle. The coated stents and bare metal stents (controls) were implanted in porcine coronary arteries, where they remained for twenty-eight days.

Angiography was performed on the pigs at implantation and at twenty-eight days. Angiography indicated that the control uncoated stent exhibited about twenty-one percent restenosis. The polyfluoro copolymer "as received" exhibited about twenty-six percent restenosis (equivalent to the control) and the washed copolymer exhibited about 12.5 percent restenosis.

Histology results reported neointimal area at twenty-eight days to be 2.89±0.2, 3.57±0.4 and 2.75±0.3, respectively, for the bare metal control, the unpurified copolymer and the purified copolymer.

Since rapamycin acts by entering the surrounding tissue, it is preferably only affixed to the surface of the stent making contact with one tissue. Typically, only the outer surface of the stent makes contact with the tissue. Accordingly, in one exemplary embodiment, only the outer surface of the stent is coated with rapamycin.

The circulatory system, under normal conditions, has to be self-sealing, otherwise continued blood loss from an injury would be life threatening. Typically, all but the most catastrophic bleeding is rapidly stopped though a process known as hemostasis. Hemostasis occurs through a progression of steps. At high rates of flow, hemostasis is a combination of events involving platelet aggregation and fibrin formation.

Platelet aggregation leads to a reduction in the blood flow due to the formation of a cellular plug while a cascade of biochemical steps leads to the formation of a fibrin clot.

Fibrin clots, as stated above, form in response to injury. There are certain circumstances where blood clotting or clotting in a specific area may pose a health risk. For example, during percutaneous transluminal coronary angioplasty, the endothelial cells of the arterial walls are typically injured, thereby exposing the sub-endothelial cells. Platelets adhere to these exposed cells. The aggregating platelets and the damaged tissue initiate further biochemical process resulting in blood coagulation. Platelet and fibrin blood clots may prevent the normal flow of blood to critical areas. Accordingly, there is a need to control blood clotting in various medical procedures. Compounds that do not allow blood to clot are called anti-coagulants. Essentially, an anti-coagulant is an inhibitor of thrombin formation or function. These compounds include drugs such as heparin and hirudin. As used herein, heparin includes all direct or indirect inhibitors of thrombin or Factor Xa.

In addition to being an effective anti-coagulant, heparin has also been demonstrated to inhibit smooth muscle cell growth in vivo. Thus, heparin may be effectively utilized in conjunction with rapamycin in the treatment of vascular disease. Essentially, the combination of rapamycin and heparin may inhibit smooth muscle cell growth via two different mechanisms in addition to the heparin acting as an anti-coagulant.

Because of its multifunctional chemistry, heparin may be immobilized or affixed to a stent in a number of ways. For example, heparin may be immobilized onto a variety of surfaces by various methods, including the photolink methods set forth in U.S. Pat. Nos. 3,959,078 and 4,722,906 to Guire et al. and U.S. Pat. Nos. 5,229,172; 5,308,641; 5,350,800 and 5,415,938 to Cahalan et al. Heparinized surfaces have also been achieved by controlled release from a polymer matrix, for example, silicone rubber, as set forth in U.S. Pat. Nos. 5,837,313; 6,099,562 and 6,120,536 to Ding et al.

In one exemplary embodiment, heparin may be immobilized onto the stent as briefly described below. The surface onto which the heparin is to be affixed is cleaned with ammonium peroxidisulfate. Once cleaned, alternating layers of polyethylenimine and dextran sulfate are deposited thereon. Preferably, four layers of the polyethylenimine and dextran sulfate are deposited with a final layer of polyethylenimine. Aldehyde-end terminated heparin is then immobilized to this final layer and stabilized with sodium cyanoborohydride. This process is set forth in U.S. Pat. Nos. 4,613,665; 4,810,784 to Larm and 5,049,403 to Larm et al.

Unlike rapamycin, heparin acts on circulating proteins in the blood and heparin need only make contact with blood to be effective. Accordingly, if used in conjunction with a medical device, such as a stent, it would preferably be only on the side that comes into contact with the blood. For example, if heparin were to be administered via a stent, it would only have to be on the inner surface of the stent to be effective.

Figure 7:
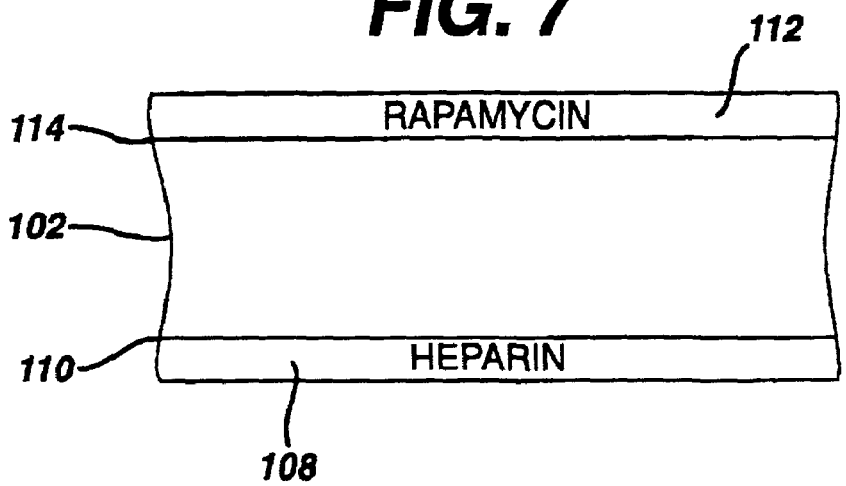
FIG. 7 is a cross-sectional view of a band of the stent of FIG. 1 having drug coatings thereon in accordance with a first exemplary embodiment of the invention.

In an exemplary embodiment of the invention, a stent may be utilized in combination with rapamycin and heparin to treat vascular disease. In this exemplary embodiment, the heparin is immobilized to the inner surface of the stent so that it is in contact with the blood and the rapamycin is immobilized to the outer surface of the stent so that it is in contact with the surrounding tissue. FIG. 7 illustrates a cross-section of a band 102 of the stent 100 illustrated in FIG. 1. As illustrated, the band 102 is coated with heparin 108 on its inner surface 110 and with rapamycin 112 on its outer surface 114.

Figure 8:
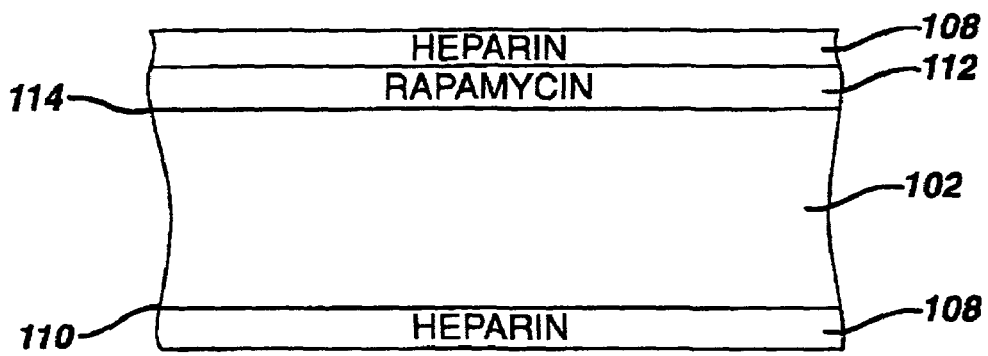
FIG. 8 is a cross-sectional view of a band of the stent of FIG. 1 having drug coatings thereon in accordance with a second exemplary embodiment of the invention.

In an alternate exemplary embodiment, the stent may comprise a heparin layer immobilized on its inner surface, and rapamycin and heparin on its outer surface. Utilizing current coating techniques, heparin tends to form a stronger bond with the surface it is immobilized to then does rapamycin. Accordingly, it may be possible to first immobilize the rapamycin to the outer surface of the stent and then immobilize a layer of heparin to the rapamycin layer. In this embodiment, the rapamycin may be more securely affixed to the stent while still effectively eluting from its polymeric matrix, through the heparin and into the surrounding tissue. FIG. 8 illustrates a cross-section of a band 102 of the stent 100 illustrated in FIG. 1. As illustrated, the band 102 is coated with heparin 108 on its inner surface 110 and with rapamycin 112 and heparin 108 on its outer surface 114.

Figure 9:
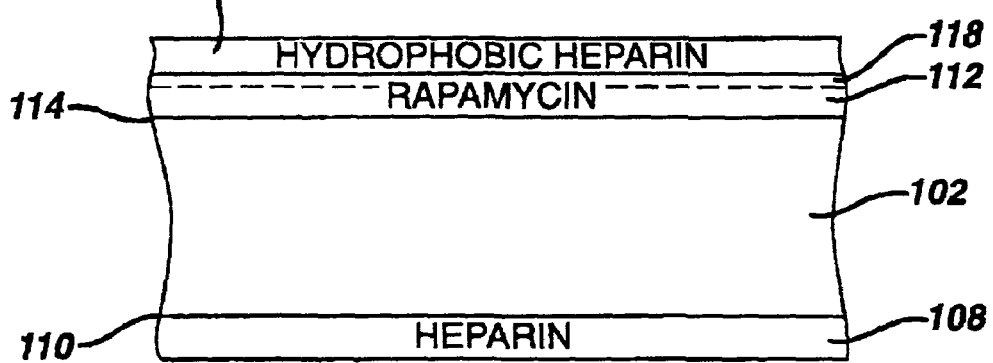
FIG. 9 is a cross-sectional view of a band of the stent of FIG. 1 having drug coatings thereon in accordance with a third exemplary embodiment of the present invention.
Figure 10:
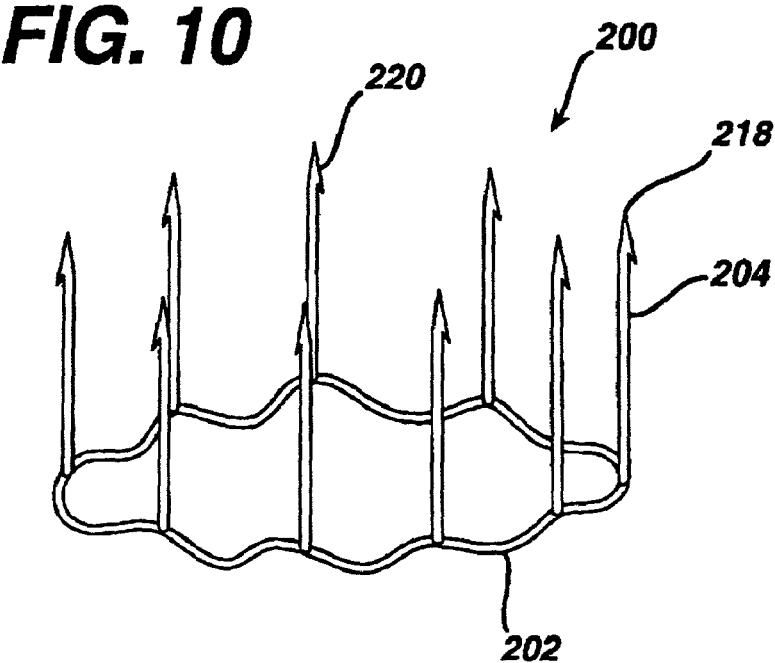
FIGS. 10-13 illustrate an exemplary one-piece embodiment of an anastomosis device having a fastening flange and attached staple members in accordance with the present invention.
Figure 11:
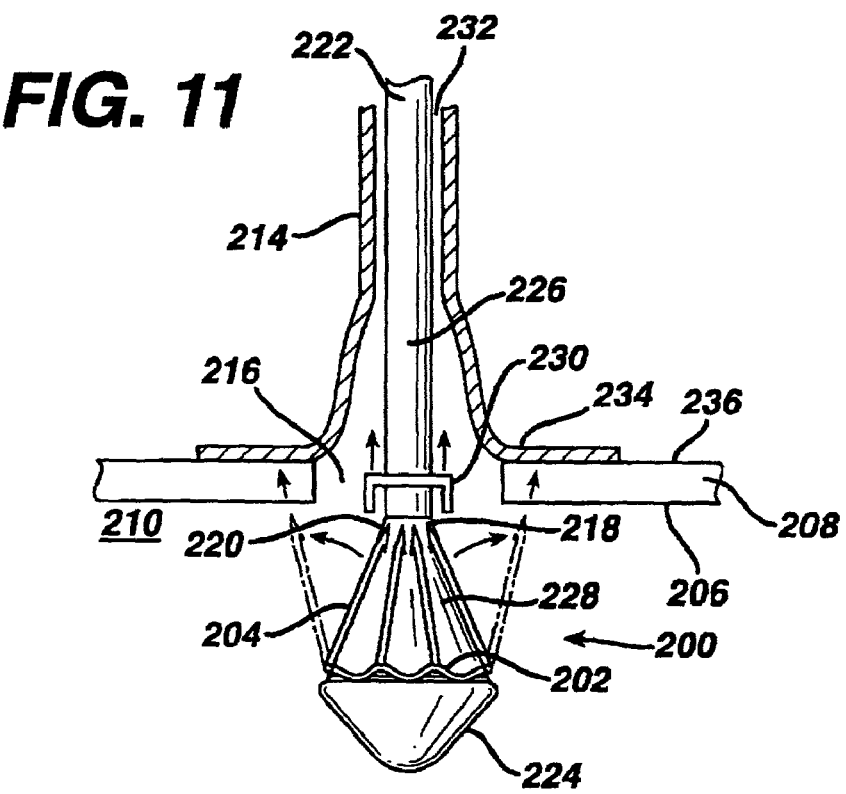
Figure 12:
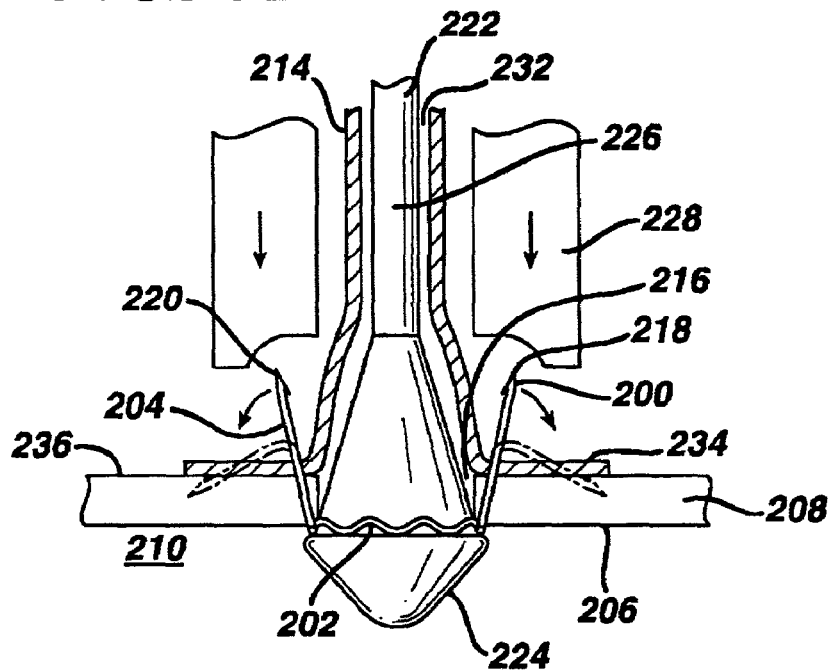
Figure 13:
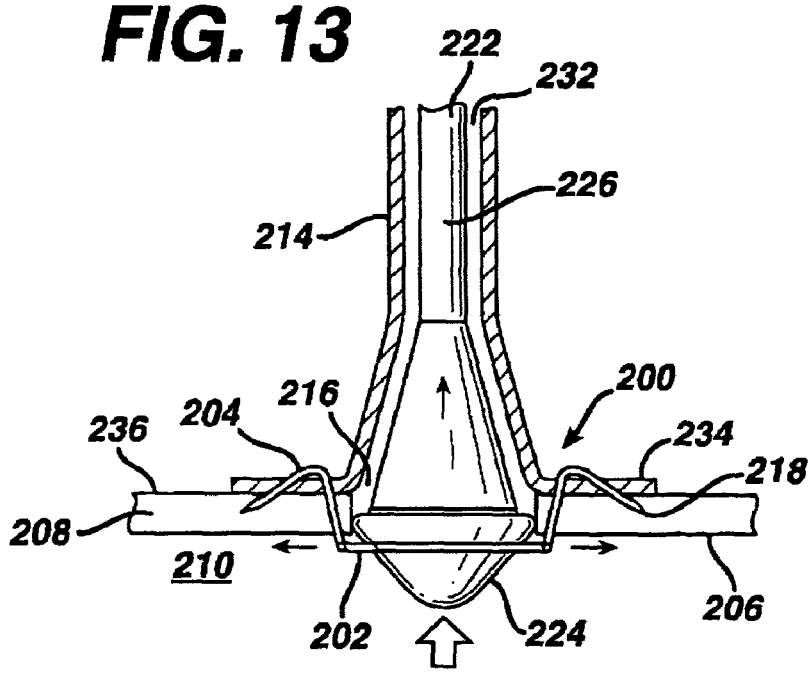

There are a number of possible ways to immobilize, i.e., entrapment or covalent linkage with an erodible bond, the heparin layer to the rapamycin layer. For example, heparin may be introduced into the top layer of the polymeric matrix. In other embodiments, different forms of heparin may be directly immobilized onto the top coat of the polymeric matrix, for example, as illustrated in FIG. 9. As illustrated, a hydrophobic heparin layer 116 may be immobilized onto the top coat layer 118 of the rapamycin layer 112. A hydrophobic form of heparin is utilized because rapamycin and heparin coatings represent incompatible coating application technologies. Rapamycin is an organic solvent-based coating and heparin, in its native form, is a water-based coating.

As stated above, a rapamycin coating may be applied to stents by a dip, spray or spin coating method, and/or any combination of these methods. Various polymers may be utilized. For example, as described above, poly(ethylene-co-vinyl acetate) and polybutyl methacrylate blends may be utilized. Other polymers may also be utilized, but not limited to, for example, polyvinylidene fluoride-co-hexafluoropropylene and polyethylbutyl methacrylate-co-hexyl methacrylate. Also as described above, barrier or top coatings may also be applied to modulate the dissolution of rapamycin from the polymer matrix. In the exemplary embodiment described above, a thin layer of heparin is applied to the surface of the polymeric matrix. Because these polymer systems are hydrophobic and incompatible with the hydrophilic heparin, appropriate surface modifications may be required.

The application of heparin to the surface of the polymeric matrix may be performed in various ways and utilizing various biocompatible materials. For example, in one embodiment, in water or alcoholic solutions, polyethylene imine may be applied on the stents, with care not to degrade the rapamycin (e.g., pH<7, low temperature), followed by the application of sodium heparinate in aqueous or alcoholic solutions. As an extension of this surface modification, covalent heparin may be linked on polyethylene imine using amide-type chemistry (using a carbondiimide activator, e.g. EDC) or reductive amination chemistry (using CBAS-heparin and sodium cyanoborohydride for coupling). In another exemplary embodiment, heparin may be photolinked on the surface, if it is appropriately grafted with photo initiator moieties. Upon application of this modified heparin formulation on the covalent stent surface, light exposure causes cross-linking and immobilization of the heparin on the coating surface. In yet another exemplary embodiment, heparin may be complexed with hydrophobic quaternary ammonium salts, rendering the molecule soluble in organic solvents (e.g. benzalkonium heparinate, troidodecylmethylammonium heparinate). Such a formulation of heparin may be compatible with the hydrophobic rapamycin coating, and may be applied directly on the coating surface, or in the rapamycin/hydrophobic polymer formulation.

It is important to note that the stent, as described above, may be formed from any number of materials, including various metals, polymeric materials and ceramic materials. Accordingly, various technologies may be utilized to immobilize the various drugs, agent, compound combinations thereon. Specifically, in addition to the polymeric matricies described above biopolymers may be utilized. Biopolymers may be generally classified as natural polymers, while the above-described polymers may be described as synthetic polymers. Exemplary biopolymers, which may be utilized include, agarose, alginate, gelatin, collagen and elastin. In addition, the drugs, agents or compounds may be utilized in conjunction with other percutaneously delivered medical devices such as grafts and profusion balloons.

In addition to utilizing an anti-proliferative and anti-coagulant, anti-inflammatories may also be utilized in combination therewith. One example of such a combination would be the addition of an anti-inflammatory corticosteroid such as dexamethasone with an anti-proliferative, such as rapamycin, cladribine, vincristine, taxol, or a nitric oxide donor and an anti-coagulant, such as heparin. Such combination therapies might result in a better therapeutic effect, i.e., less proliferation as well as less inflammation, a stimulus for proliferation, than would occur with either agent alone. The delivery of a stent comprising an anti-proliferative, anti-coagulant, and an anti-inflammatory to an injured vessel would provide the added therapeutic benefit of limiting the degree of local smooth muscle cell proliferation, reducing a stimulus for proliferation, i.e., inflammation and reducing the effects of coagulation thus enhancing the restenosis-limiting action of the stent.

In other exemplary embodiments of the inventions, growth factor inhibitor or cytokine signal transduction inhibitor, such as the ras inhibitor, R115777, or P38 kinase inhibitor, RWJ67657, or a tyrosine kinase inhibitor, such as tyrphostin, might be combined with an anti-proliferative agent such as taxol, vincristine or rapamycin so that proliferation of smooth muscle cells could be inhibited by different mechanisms. Alternatively, an anti-proliferative agent such as taxol, vincristine or rapamycin could be combined with an inhibitor of extracellular matrix synthesis such as halofuginone. In the above cases, agents acting by different mechanisms could act synergistically to reduce smooth muscle cell proliferation and vascular hyperplasia. This invention is also intended to cover other combinations of two or more such drug agents. As mentioned above, such drugs, agents or compounds could be administered systemically, delivered locally via drug delivery catheter, or formulated for delivery from the surface of a stent, or given as a combination of systemic and local therapy.

In addition to anti-proliferatives, anti-inflammatories and anti-coagulants, other drugs, agents or compounds may be utilized in conjunction with the medical devices. For example, immunosuppressants may be utilized alone or in combination with these other drugs, agents or compounds. Also gene therapy delivery mechanisms such as modified genes (nucleic acids including recombinant DNA) in viral vectors and non-viral gene vectors such as plasmids may also be introduced locally via a medical device. In addition, the present invention may be utilized with cell based therapy.

In addition to all of the drugs, agents, compounds and modified genes described above, chemical agents that are not ordinarily therapeutically or biologically active may also be utilized in conjunction with the present invention. These chemical agents, commonly referred to as pro-drugs, are agents that become biologically active upon their introduction into the living organism by one or more mechanisms. These mechanisms include the addition of compounds supplied by the organism or the cleavage of compounds from the agents caused by another agent supplied by the organism. Typically, pro-drugs are more absorbable by the organism. In addition, pro-drugs may also provide some additional measure of time release.

The coatings and drugs, agents or compounds described above may be utilized in combination with any number of medical devices, and in particular, with implantable medical devices such as stents and stent-grafts. Other devices such as vena cava filters and anastomosis devices may be used with coatings having drugs, agents or compounds therein. The exemplary stent illustrated in FIGS. 1 and 2 is a balloon expandable stent. Balloon expandable stents may be utilized in any number of vessels or conduits, and are particularly well suited for use in coronary arteries. Self-expanding stents, on the other hand, are particularly well suited for use in vessels where crush recovery is a critical factor, for example, in the carotid artery. Accordingly, it is important to note that any of the drugs, agents or compounds, as well as the coatings described above, may be utilized in combination with self-expanding stents which are known in the art.

Anastomosis is the surgical joining of biological tissues, specifically the joining of tubular organs to create an intercommunication between them. Vascular surgery often involves creating an anastomosis between blood vessels or between a blood vessel and a vascular graft to create or restore a blood flow path to essential tissues. Coronary artery bypass graft surgery (CABG) is a surgical procedure to restore blood flow to ischemic heart muscle whose blood supply has been compromised by occlusion or stenosis of one or more of the coronary arteries. One method for performing CABG surgery involves harvesting a saphenous vein or other venous or arterial conduit from elsewhere in the body, or using an artificial conduit, such as one made of Dacron® or Goretex® tubing, and connecting this conduit as a bypass graft from a viable artery, such as the aorta, to the coronary artery downstream of the blockage or narrowing. A graft with both the proximal and distal ends of the graft detached is known as a "free graft." A second method involves rerouting a less essential artery, such as the internal mammary artery, from its native location so that it may be connected to the coronary artery downstream of the blockage. The proximal end of the graft vessel remains attached in its native position. This type of graft is known as a "pedicled graft." In the first case, the bypass graft must be attached to the native arteries by an end-to-side anastomosis at both the proximal and distal ends of the graft. In the second technique at least one end-to-side anastomosis must be made at the distal end of the artery used for the bypass. In the description of the exemplary embodiment given below reference will be made to the anastomoses on a free graft as the proximal anastomosis and the distal anastomosis. A proximal anastomosis is an anastomosis on the end of the graft vessel connected to a source of blood, for example, the aorta and a distal anastomosis is an anastomosis on the end of the graft vessel connected to the destination of the blood flowing through it, for example, a coronary artery. The anastomoses will also sometimes be called the first anastomosis or second anastomosis, which refers to the order in which the anastomoses are performed regardless of whether the anastomosis is on the proximal or distal end of the graft.

At present, essentially all vascular anastomoses are performed by conventional hand suturing. Suturing the anastomoses is a time-consuming and difficult task, requiring much skill and practice on the part of the surgeon. It is important that each anastomosis provide a smooth, open flow path for the blood and that the attachment be completely free of leaks. A completely leak-free seal is not always achieved on the very first try. Consequently, there is a frequent need for resuturing of the anastomosis to close any leaks that are detected.

The time consuming nature of hand sutured anastomoses is of special concern in CABG surgery for several reasons. Firstly, the patient is required to be supported on cardiopulmonary bypass (CPB) for most of the surgical procedure, the heart must be isolated from the systemic circulation (i.e. "cross-clamped"), and the heart must usually be stopped, typically by infusion of cold cardioplegia solution, so that the anastomosis site on the heart is still and blood-free during the suturing of the anastomosis. Cardiopulminary bypass, circulatory isolation and cardiac arrest are inherently very traumatic, and it has been found that the frequency of certain post-surgical complications varies directly with the duration for which the heart is under cardioplegic arrest (frequently referred to as the "crossclamp time"). Secondly, because of the high cost of cardiac operating room time, any prolongation of the surgical procedure can significantly increase the cost of the bypass operation to the hospital and to the patient. Thus, it is desirable to reduce the duration of the crossclamp time and of the entire surgery by expediting the anastomosis procedure without reducing the quality or effectiveness of the anastomoses.

The already high degree of manual skill required for conventional manually sutured anastomoses is even more elevated for closed-chest or port-access thoracoscopic bypass surgery, a newly developed surgical procedure designed to reduce the morbidity of CABG surgery as compared to the standard open-chest CABG procedure. In the closed-chest procedure, surgical access to the heart is made through narrow access ports made in the intercostal spaces of the patient's chest, and the procedure is performed under thoracoscopic observation. Because the patient's chest is not opened, the suturing of the anastomoses must be performed at some distance, using elongated instruments positioned through the access ports for approximating the tissues and for holding and manipulating the needles and sutures used to make the anastomoses. This requires even greater manual skill than the already difficult procedure of suturing anastomoses during open-chest CABG surgery.

In order to reduce the difficulty of creating the vascular anastomoses during either open or closed-chest CABG surgery, it would be desirable to provide a rapid means for making a reliable end-to-side anastomosis between a bypass graft or artery and the aorta or the native vessels of the heart. A first approach to expediting and improving anastomosis procedures has been through stapling technology. Stapling technology has been successfully employed in many different areas of surgery for making tissue attachments faster and more reliably. The greatest progress in stapling technology has been in the area of gastrointestinal surgery. Various surgical stapling instruments have been developed for end-to-end, side-to-side, and end-to-side anastomoses of hollow or tubular organs, such as the bowel. These instruments, unfortunately, are not easily adaptable for use in creating vascular anastomoses. This is partially due to the difficulty in miniaturizing the instruments to make them suitable for smaller organs such as blood vessels. Possibly even more important is the necessity of providing a smooth, open flow path for the blood. Known gastrointestinal stapling instruments for end-to-side or end-to-end anastomosis of tubular organs are designed to create an inverted anastomosis, that is, one where the tissue folds inward into the lumen of the organ that is being attached. This is acceptable in gastrointestinal surgery, where it is most important to approximate the outer layers of the intestinal tract (the serosa). This is the tissue which grows together to form a strong, permanent connection. However, in vascular surgery this geometry is unacceptable for several reasons. Firstly, the inverted vessel walls would cause a disruption in the blood flow. This could cause decreased flow and ischemia downstream of the disruption, or, worse yet, the flow disruption or eddies created could become a locus for thrombosis which could shed emboli or occlude the vessel at the anastomosis site. Secondly, unlike the intestinal tract, the outer surfaces of the blood vessels (the adventitia) will not grow together when approximated. The sutures, staples, or other joining device may therefore be needed permanently to maintain the structural integrity of the vascular anastomosis. Thirdly, to establish a permanent, nonthrombogenic vessel, the innermost layer (the endothelium) should grow together for a continuous, uninterrupted lining of the entire vessel. Thus, it would be preferable to have a stapling instrument that would create vascular anastomoses that are everted, that is folded outward, or which create direct edge-to-edge coaptation without inversion.

At least one stapling instrument has been applied to performing vascular anastomoses during CABG surgery. This device, first adapted for use in CABG surgery by Dr. Vasilii I. Kolesov and later refined by Dr. Evgenii V. Kolesov (U.S. Pat. No. 4,350,160), was used to create an end-to-end anastomosis between the internal mammary artery (IMA) or a vein graft and one of the coronary arteries, primarily the left anterior descending coronary artery (LAD). Because the device could only perform end-to-end anastomoses, the coronary artery first had to be severed and dissected from the surrounding myocardium, and the exposed end everted for attachment. This technique limited the indications of the device to cases where the coronary artery was totally occluded, and therefore there was no loss of blood flow by completely severing the coronary artery downstream of the blockage to make the anastomosis. Consequently, this device is not applicable where the coronary artery is only partially occluded and is not at all applicable to making the proximal side-to-end anastomosis between a bypass graft and the aorta.

One attempt to provide a vascular stapling device for end-to-side vascular anastomoses is described in U.S. Pat. No. 5,234,447, issued to Kaster et al. for a Side-to-end Vascular Anastomotic Staple Apparatus. Kaster et al. provide a ring-shaped staple with staple legs extending from the proximal and distal ends of the ring to join two blood vessels together in an end-to-side anastomosis. However, Kaster et al. does not provide a complete system for quickly and automatically performing an anastomosis. The method of applying the anastomosis staple disclosed by Kaster et al. involves a great deal of manual manipulation of the staple, using hand operated tools to individually deform the distal tines of the staple after the graft has been attached and before it is inserted into the opening made in the aortic wall. One of the more difficult maneuvers in applying the Kaster et al. staple involves carefully everting the graft vessel over the sharpened ends of the staple legs, then piercing the evened edge of the vessel with the staple legs. Experimental attempts to apply this technique have proven to be very problematic because of difficulty in manipulating the graft vessel and the potential for damage to the graft vessel wall. For speed, reliability and convenience, it is preferable to avoid the need for complex maneuvers while performing the anastomosis. Further bending operations must then be performed on the staple legs. Once the distal tines of the staple have been deformed, it may be difficult to insert the staple through the aortotomy opening. Another disadvantage of the Kaster et al. device is that the distal tines of the staple pierce the wall of the graft vessel at the point where it is evened over the staple. Piercing the wall of the graft vessel potentially invites leaking of the anastomosis and may compromise the structural integrity of the graft vessel wall, serving as a locus for a dissection or even a tear which could lead to catastrophic failure. Because the Kaster et al staple legs only apply pressure to the anastomosis at selected points, there is a potential for leaks between the staple legs. The distal tines of the staple are also exposed to the blood flow path at the anastomotic site where it is most critical to avoid the potential for thrombosis. There is also the potential that exposure of the medial layers of the graft vessel where the staple pierces the wall could be a site for the onset of intimal hyperplasia, which would compromise the long-term patency of the graft as described above. Because of these potential drawbacks, it is desirable to make the attachment to the graft vessel as atraumatic to the vessel wall as possible and to eliminate as much as possible the exposure of any foreign materials or any vessel layers other than a smooth uninterrupted intimal layer within the anastomosis site or within the graft vessel lumen.

A second approach to expediting and improving anastomosis procedures is through the use of anastomotic fittings for joining blood vessels together. One attempt to provide a vascular anastomotic fitting device for end-to-side vascular anastomoses is described in U.S. Pat. No. 4,366,819, issued to Kaster for an Anastomotic Fitting. This device is a four-part anastomotic fitting having a tubular member over which the graft vessel is evened, a ring flange which engages the aortic wall from within the aortic lumen, and a fixation ring and a locking ring which engage the exterior of the aortic wall. Another similar Anastomotic Fitting is described in U.S. Pat. No. 4,368,736, also issued to Kaster. This device is a tubular fitting with a flanged distal end that fastens to the aortic wall with an attachment ring, and a proximal end with a graft fixation collar for attaching to the graft vessel. These devices have a number of drawbacks. Firstly, the anastomotic fittings described expose the foreign material of the anastomotic device to the blood flow path within the arteries. This is undesirable because foreign materials within the blood flow path can have a tendency to cause hemolysis, platelet deposition and thrombosis. Immune responses to foreign material, such as rejection of the foreign material or auto-immune responses triggered by the presence of foreign material, tend to be stronger when the material is exposed to the bloodstream. As such, it is preferable that as much as possible of the interior surfaces of an anastomotic fitting that will be exposed to the blood flow path be covered with vascular tissue, either from the target vessel or from the graft vessel, so that a smooth, continuous, hemocompatible endothelial layer will be presented to the bloodstream. The anastomotic fitting described by Kaster in the '819 patent also has the potential drawback that the spikes that hold the graft vessel onto the anastomotic fitting are very close to the blood flow path, potentially causing trauma to the blood vessel that could lead to leaks in the anastomosis or compromise of the mechanical integrity of the vessels. Consequently, it is desirable to provide an anastomosis fitting that is as atraumatic to the graft vessel as possible. Any sharp features such as attachment spikes should be placed as far away from the blood flow path and the anastomosis site as possible so that there is no compromise of the anastomosis seal or the structural integrity of the vessels.

Another device, the 3M-Unilink device for end-to-end anastomosis (U.S. Pat. Nos. 4,624,257; 4,917,090; 4,917, 091) is designed for use in microsurgery, such as for reattaching vessels severed in accidents. This device provides an anastomosis clamp that has two eversion rings which are locked together by a series of impaling spikes on their opposing faces. However, this device is awkward for use in end-to-side anastomosis and tends to deform the target vessel; therefore it is not currently used in CABG surgery. Due to the delicate process needed to insert the vessels into the device, it would also be unsuitable for port-access surgery.

In order to solve these and other problems, it is desirable to provide an anastomosis device which performs an end-to-side anastomosis between blood vessels or other hollow organs and vessels. It is also desirable to provide an anastomosis device which minimizes the trauma to the blood vessels while performing the anastomosis, which minimizes the amount of foreign materials exposed to the blood flow path within the blood vessels and which avoids leakage problems, and which promotes rapid endothelialization and healing. It is also desirable that the invention provide a complete system for quickly and automatically performing an anastomosis with a minimal amount of manual manipulation.

Anastomosis devices may be utilized to join biological tissues, and more particularly, joining tubular organs to create a fluid channel. The connections between the tubular organs or vessels may be made side to side, end to end and/or end to side. Typically, there is a graft vessel and a target vessel. The target vessel may be an artery, vein or any other conduit or fluid carrying vessel, for example, coronary arteries. The graft vessel may comprise a synthetic material, an autologus vessel, a homologus vessel or a xenograft. Anastomosis devices may comprise any suitable biocompatible materials, for example, metals, polymers and elastomers. In addition, there are a wide variety of designs and configurations for anastomosis devices depending on the type of connection to be made. Similarly to stents, anastomosis devices cause some injury to the target vessel, thereby provoking a response from the body. Therefore, as in the case with stents, there is the potential for smooth muscle cell proliferation which can lead to blocked connections. Accordingly, there is a need to minimize or substantially eliminate smooth muscle cell proliferation and inflammation at the anastomotic site. Rapamycin and/or other drugs, agents or compounds may be utilized in a manner analogous to stents as described above. In other words, at least a portion of the anastomosis device may be coated with rapamycin or other drug, agent or compound.

FIGS. 10-13 illustrate an exemplary anastomosis device 200 for an end to side anastomosis. The exemplary anastomosis device 200 comprises a fastening flange 202 and attached staple members 204. As stated above, the anastomosis device may comprise any suitable biocomopatible material. Preferably, the anastomosis device 200 comprises a deformable biocompatible metal, such as a stainless steel alloy, a titanium alloy or a cobalt alloy. Also as stated above, a surface coating or surface coating comprising a drug, agent or compound may be utilized to improve the biocompatibility or other material characteristics of the device as well as to reduce or substantially eliminate the body's response to its placement therein.

In the exemplary embodiment, the fastening flange 202 resides on the interior surface 206 of the target vessel wall 208 when the anastomosis is completed. In order to substantially reduce the risk of hemolysis, thrombogenesis or foreign body reactions, the total mass of the fastening flange 202 is preferably as small as possible to reduce the amount of foreign material within the target vessel lumen 210.

The fastening flange 202 is in the form of a wire ring with an internal diameter, which when fully expanded, is slightly greater than the outside diameter of the graft vessel wall 214 and of the opening 216 made in the target vessel wall 208. Initially, the wire ring of the fastening flange 202 has a rippled wave-like shape to reduce the diameter of the ring so that it will easily fit through the opening 216 in the target vessel wall 208. The plurality of staple members 204 extend substantially perpendicular from the wire ring in the proximal direction. In the illustrative exemplary embodiment, there are nine staple members 204 attached to the wire ring fastening flange 202. Other variations of the anastomosis device 200 might typically have from four to twelve staple members 204 depending on the size of the vessels to be joined and the security of attachment required in the particular application. The staple members 204 may be integrally formed with the wire ring fastening flange 202 or the staple members 204 may be attached to the fastening flange 202 by welding, brazing or any other suitable joining method. The proximal ends 218 of the staple members 204 are sharpened to easily pierce the target vessel wall 208 and the graft vessel wall 214. Preferably, the proximal ends 218 of the staple members 204 have barbs 220 to improve the security of the attachment when the anastomosis device 200 is deployed. The anastomosis device 200 is prepared for use by mounting the device onto the distal end of an application instrument 222. The fastening flange 202 is mounted on an anvil 224 attached to the distal end of the elongated shaft 226 of the application instrument 222. The staple members 204 are compressed inward against a conical holder 228 attached to the instrument 222 proximal to the anvil 224. The staple members 204 are secured in this position by a cap 230 which is slidably mounted on the elongated shaft 226. The cap 230 moves distally to cover the sharpened, barbed proximal ends 218 of the staple members 204 and to hold them against the conical holder 228. The application instrument 222 is then inserted through the lumen 232 of the graft vessel 214. This may be done by inserting the application instrument 222 through the graft vessel lumen 232 from the proximal to the distal end of the graft vessel 214, or it may be done by backloading the elongated shaft 226 of the application instrument 222 into the graft vessel lumen 232 from the distal end to the proximal end, whichever is most convenient in the case. The anvil 224 and conical holder 228 on the distal end of the application instrument 222 with the anastomosis device 200 attached is extended through the opening 216 into the lumen 210 of the target vessel.

Next, the distal end 234 of the graft vessel wall 214 is everted against the exterior surface 236 of the target vessel wall 208 with the graft vessel lumen 232 centered over the opening 216 in the target vessel wall 208. The cap 230 is withdrawn from the proximal ends 218 of the staple members 204, allowing the staple members 204 to spring outward to their expanded position. The application instrument 222 is then drawn in the proximal direction so that the staple members pierce the target vessel wall 208 surrounding the opening 216 and the everted distil end 234 of the graft vessel 214.

The application instrument 222 has an annular staple former 238 which surrounds the outside of the graft vessel 214. Slight pressure on the everted graft vessel wall from the annular staple former 238 during the piercing step assists in piercing the staple members 204 through the graft vessel wall 214. Care should be taken not to apply too much pressure with the annular staple former 238 at this point in the process because the staple members 204 could be prematurely deformed before they have fully traversed the vessel walls. If desired, an annular surface made of a softer material, such as an elastomer, can be provided on the application instrument 222 to back up the vessel walls as the staple members 204 pierce through them.

Once the staple members 204 have fully traversed the target vessel wall 208 and the graft vessel wall 214, the staple former 238 is brought down with greater force while supporting the fastening flange 202 with the anvil 224. The staple members 204 are deformed outward so that the sharpened, barbed ends 218 pierce back through the everted distil end 234 and into the target vessel wall 208 to form a permanent attachment. To complete the anastomosis, the anvil 224 is withdrawn through the graft vessel lumen 232. As the anvil 224 passes through the wire ring fastening flange 202, it straightens out the wave-like ripples so that the wire ring flange 202 assumes its full expanded diameter. Alternately, the wire ring fastening flange 202 may be made of a resilient material so that the flange 202 may be compressed and held in a rippled or folded position until it is released within the target vessel lumen 210, whereupon it will resume its full expanded diameter. Another alternate construction would be to move the anastomosis device of a shape-memory alloy so that the fastening flange may be compressed and inserted through the opening in the target vessel, whereupon it would be returned to its full expanded diameter by heating the device 200 to a temperature above the shape-memory transition temperature.

In the above-described exemplary embodiment, the staple members 204 and/or the wire ring fastening flange 202 may be coated with any of the above-described agents, drugs or compounds such as rapamycin to prevent or substantially reduce smooth muscle wall proliferation.

Figure 14:
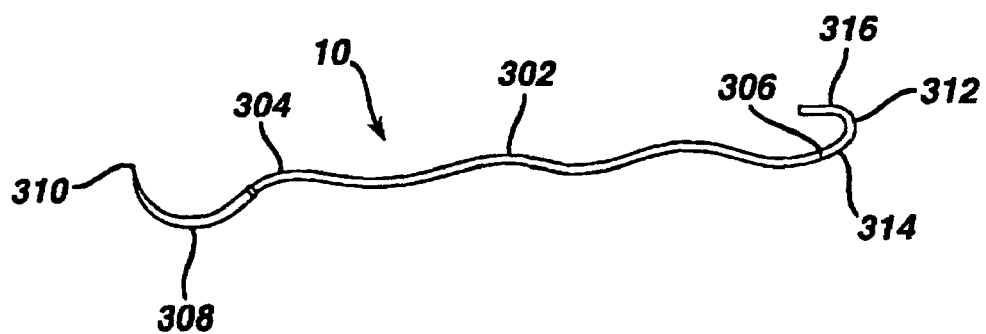
FIG. 14 is a side view of an apparatus for joining anatomical structures together, according to an embodiment of the invention.

FIG. 14 illustrates an alternate exemplary embodiment of an anastomosis device. FIG. 14 is a side view of an apparatus for joining at least two anatomical structures, according to another exemplary embodiment of the present invention. Apparatus 300 includes a suture 302 having a first end 304 and a second end 306, the suture 302 being constructed for passage through anatomical structures in a manner to be described subsequently. Suture 302 may be formed from a wide variety of materials, for example, monofilament materials having minimal memory, including polypropylene or polyamide. Any appropriate diameter size may be used, for example, through 8-0. Other suture types and sizes are also possible, of course, and are equally contemplated by the present invention.

A needle 308 preferably is curved and is disposed at the first end 304 of the suture 302. A sharp tip 310 of needle 308 enables easy penetration of various anatomical structures and enables the needle 308 and the suture 302 to readily pass therethrough. The needle 308 may be attached to the suture 302 in various ways, for example, by swedging, preferably substantially matching the outer diameter of the needle 308 and the suture 302 as closely as possible.

Apparatus 300 also includes a holding device 312 disposed at the second end 306 of the suture 302. The holding device 312 includes first and second limbs 314, 316, according to the illustrated exemplary embodiment, and preferably is of greater stiffness than the suture 302. The first limb 314 may be connected to suture 302 in a number of ways, for example, by swedging, preferably substantially matching the outside diameter of the suture 302 and the holding device 312 as closely as possible. The holding device 312 includes a staple structure comprising a bendable material that preferably is soft and malleable enough to crimp and hold its crimped position on the outside of an anastomosis. Such materials may include titanium or stainless steel. The holding device 312 may be referred to as a staple, according to the illustrated embodiment, and the suture 302 and the needle 308 a delivery system for staple 312.

FIG. 14 illustrates one of the many possible initial configurations of holding device 312, i.e. the configuration the holding device 312 is in upon initial passage through the anatomical structures and/or at a point in time beforehand. As will be described, the holding device 312 is movable from the initial configuration to a holding configuration, in which holding device 312 holds the anatomical structures together. According to the illustrated exemplary embodiments, the holding device 312 assumes the holding configuration when it is bent or crimped, as shown in FIG. 19 (further described below).

The holding device 312 preferably is substantially V-shaped or substantially U-shaped, as illustrated, but may assume a wide variety of shapes to suit particular surgical situations and/or surgeon preference. For example, one of limbs 314, 316 may be straight and the other curved, or limbs 314, 316 may be collinear. The holding device 312 preferably is as smooth and round in cross-section as the needle 308. Further, the diameters of the needle 308, the suture 302, and the holding device 312 preferably are substantially identical, especially the needle 308 and the holding device 312, to avoid creating holes in the anatomical structures that are larger than the diameter of the staple 312. Such holes likely would cause bleeding and/or leakage.

Figure 15:
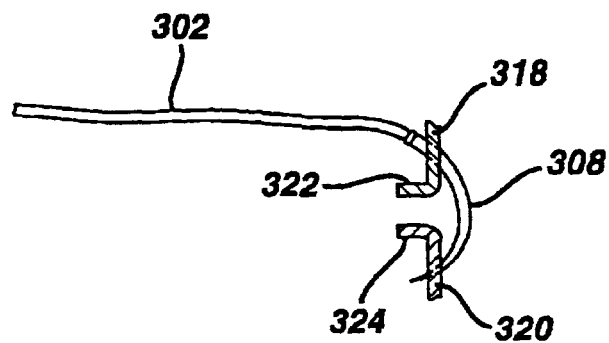
FIG. 15 is a cross-sectional view showing a needle portion of the FIG. 14 apparatus passing through edges of anatomical structures, according to an embodiment of the invention.
Figure 16:
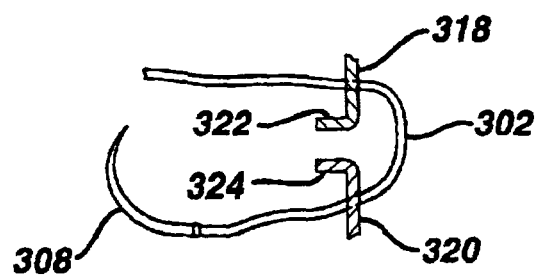
FIG. 16 is a cross-sectional view showing the FIG. 14 apparatus pulled through an anastomosis, according to an embodiment of the invention.
Figure 17:
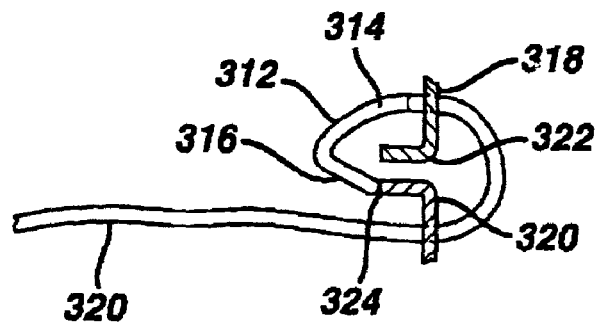
FIG. 17 is a cross-sectional view showing a staple of the FIG. 14 apparatus being placed into proximity with the anatomical structures, according to an embodiment of the invention
Figure 18:
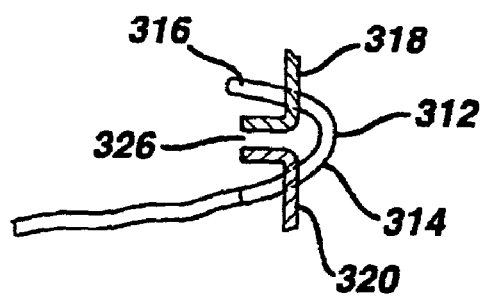
FIG. 18 is a cross-sectional view showing a staple of the FIG. 14 apparatus being engaged on both sides of the anastomosis, according to an embodiment of the invention.
Figure 19:
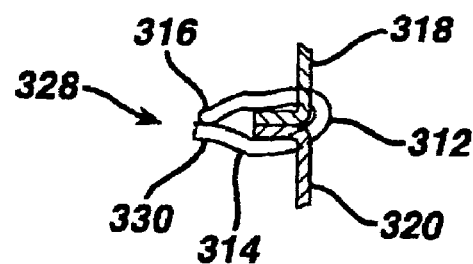
FIG. 19 is a cross-sectional view showing a staple after it has been crimped to join the anatomical structures, according to an embodiment of the invention.

A method of using apparatus 300 is illustrated in FIGS. 15-19. First, as illustrated in FIG. 15, the needle 308 passes through anatomical structures 318, 320, which are, for example, vascular structures. Specifically, according to the illustrated exemplary embodiment, the needle 308 passes through the edges 322, 324 of vascular structures 318, 320. Then, as shown in FIG. 16, the needle 308 pulls suture 302 into and through both structures 318, 320. The staple 312 then is pulled into desired proximity with structures 318, 320, as shown in FIGS. 17-19, such that it is engaged on both sides of the illustrated anastomosis and associated lumen 326. According to one exemplary embodiment, traction is placed on suture 302 to hook staple 312 into position.

As illustrated in FIG. 19 and as referenced earlier, the staple 312 then is moved from its initial configuration to a holding or crimped configuration 328, in which anatomical structures 318, 320 are joined together to effect an anastomosis between them. The staple 312 creates a substantially three hundred sixty-degree loop at the edge of the anastomosis, with crimped portion 330 outside lumen 321. A wide variety of tools and/or mechanisms may be used to crimp the staple 312 into its holding configuration, for example, in the manner of closure of a vascular clip. The same tool, or an alternative tool, may then be used to separate the staple 312 from the suture 302, for example, by cutting.

Thus, the staple 312 holds vascular structures 318, 320 together from inside the vascular structures, as well as from outside, unlike the many prior art staples that secure opposed structures only externally. This achieves a number of advantages, as described above. Not only does a better approximation result, but crimping a staple is simpler than tying one or more knots and is also less likely traumatic on tissue. Staple closure with a single crimp provides less tension on an anastomosis, for example, than a knot requiring several throws. Embodiments of the invention are especially advantageous in minimally invasive surgical situations, as knot-tying with, for example, a knot pusher in a minimally invasive setting through a small port is particularly tedious and can require up to four or five throws to prevent slippage. Crimping a staple through the port, as with embodiments of the invention, is far simpler and eliminates much of the difficulty.

According to one exemplary embodiment, the surgeon achieves a precise approximation of the vascular or other structures with preferably a limited number of staples or other holding devices, and then completes the anastomosis with biologic glue or laser techniques. The holding devices, for example, two or more in number, may be used to orient or line up the structures initially and thus used as a "pilot" for guiding the completion of the anastomosis.

In the above described exemplary embodiment, the holding device 312 may be coated with any of the above-described drugs, agents or compounds such as rapamycin to prevent or substantially reduce smooth muscle cell proliferation.

As described above, various drugs, agents or compounds may be locally delivered via medical devices. For example, rapamycin and heparin may be delivered by a stent to reduce restenosis, inflammation, and coagulation. Various techniques for immobilizing the drugs, agents or compounds are discussed above, however, maintaining the drugs, agents or compounds on the medical devices during delivery and positioning is critical to the success of the procedure or treatment. For example, removal of the drug, agent or compound coating during delivery of the stent can potentially cause failure of the device. For a self-expanding stent, the retraction of the restraining sheath may cause the drugs, agents or compounds to rub off the stent. For a balloon expandable stent, the expansion of the balloon may cause the drugs, agents or compounds to simply delaminate from the stent through contact with the balloon or via expansion. Therefore, prevention of this potential problem is important to have a successful therapeutic medical device, such as a stent.

There are a number of approaches that may be utilized to substantially reduce the above-described concern. In one exemplary embodiment, a lubricant or mold release agent may be utilized. The lubricant or mold release agent may comprise any suitable biocompatible lubricious coating. An exemplary lubricious coating may comprise silicone. In this exemplary embodiment, a solution of the silicone base coating may be introduced onto the balloon surface, onto the polymeric matrix, and/or onto the inner surface of the sheath of a self-expanding stent delivery apparatus and allowed to air cure. Alternately, the silicone based coating may be incorporated into the polymeric matrix. It is important to note, however, that any number of lubricious materials may be utilized, with the basic requirements being that the material be biocompatible, that the material not interfere with the actions/effectiveness of the drugs, agents or compounds and that the material not interfere with the materials utilized to immobilize the drugs, agents or compounds on the medical device. It is also important to note that one or more, or all of the above-described approaches may be utilized in combination.

Figure 20:
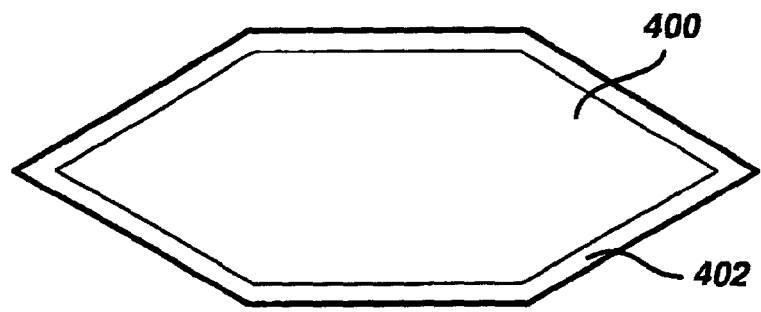
FIG. 20 is a cross-sectional view of a balloon having a lubricious coating affixed thereto in accordance with the present invention.

Referring now to FIG. 20, there is illustrated a balloon 400 of a balloon catheter that may be utilized to expand a stent in situ. As illustrated, the balloon 400 comprises a lubricious coating 402. The lubricious coating 402 functions to minimize or substantially eliminate the adhesion between the balloon 400 and the coating on the medical device. In the exemplary embodiment described above, the lubricious coating 402 would minimize or substantially eliminate the adhesion between the balloon 400 and the heparin or rapamycin coating. The lubricious coating 402 may be attached to and maintained on the balloon 400 in any number of ways including but not limited to dipping, spraying, brushing or spin coating of the coating material from a solution or suspension followed by curing or solvent removal step as needed.

Materials such as synthetic waxes, e.g. diethyleneglycol monostearate, hydrogenated castor oil, oleic acid, stearic acid, zinc stearate, calcium stearate, ethylenebis (stearamide), natural products such as paraffin wax, spermaceti wax, carnuba wax, sodium alginate, ascorbic acid and flour, fluorinated compounds such as perfluoroalkanes, perfluorofatty acids and alcohol, synthetic polymers such as silicones e.g. polydimethylsiloxane, polytetrafluoroethylene, polyfluoroethers, polyalkylglycol e.g. polyethylene glycol waxes, and inorganic materials such as talc, kaolin, mica, and silica may be used to prepare these coatings. Vapor deposition polymerization e.g. parylene-C deposition, or RF-plasma polymerization of perfluoroalkenes and perfluoroalkanes can also be used to prepare these lubricious coatings.

Figure 21:
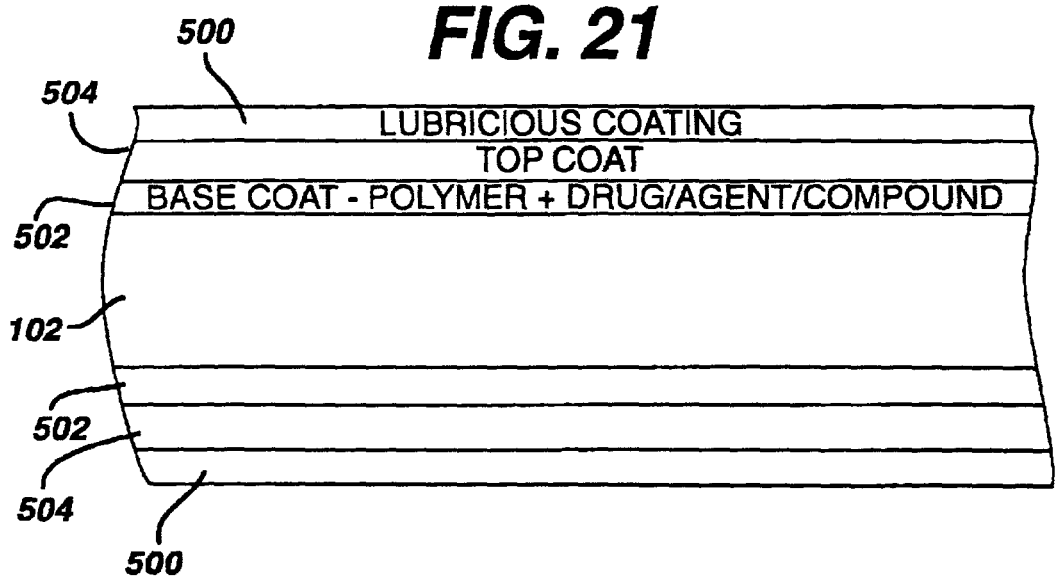
FIG. 21 is a cross-sectional view of a band of the stent in FIG. 1 having a lubricious coating affixed thereto in accordance with the present invention.

FIG. 21 illustrates a cross-section of a band 102 of the stent 100 illustrated in FIG. 1. In this exemplary embodiment, the lubricious coating 500 is immobilized onto the outer surface of the polymeric coating. As described above, the drugs, agents or compounds may be incorporated into a polymeric matrix. The stent band 102 illustrated in FIG. 21 comprises a base coat 502 comprising a polymer and rapamycin and a top coat 504 or diffusion layer 504 also comprising a polymer. The lubricious coating 500 is affixed to the top coat 502 by any suitable means, including but not limited to spraying, brushing, dipping or spin coating of the coating material from a solution or suspension with or without the polymers used to create the top coat, followed by curing or solvent removal step as needed. Vapor deposition polymerization and RF-plasma polymerization may also be used to affix those lubricious coating materials that lend themselves to this deposition method, to the top coating. In an alternate exemplary embodiment, the lubricious coating may be directly incorporated into the polymeric matrix.

Figure 22:
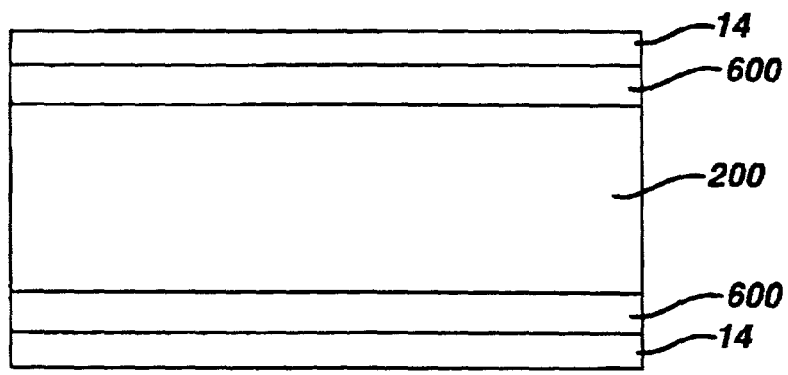
FIG. 22 is a cross-sectional view of a self-expanding stent in a delivery device having a lubricious coating in accordance with the present invention.

If a self-expanding stent is utilized, the lubricious coating may be affixed to the inner surface of the restraining sheath. FIG. 22 illustrates a self-expanding stent 200 within the lumen of a delivery apparatus sheath 14. As illustrated, a lubricious coating 600 is affixed to the inner surfaces of the sheath 14. Accordingly, upon deployment of the stent 200, the lubricious coating 600 preferably minimizes or substantially eliminates the adhesion between the sheath 14 and the drug, agent or compound coated stent 200.

Figure 23:
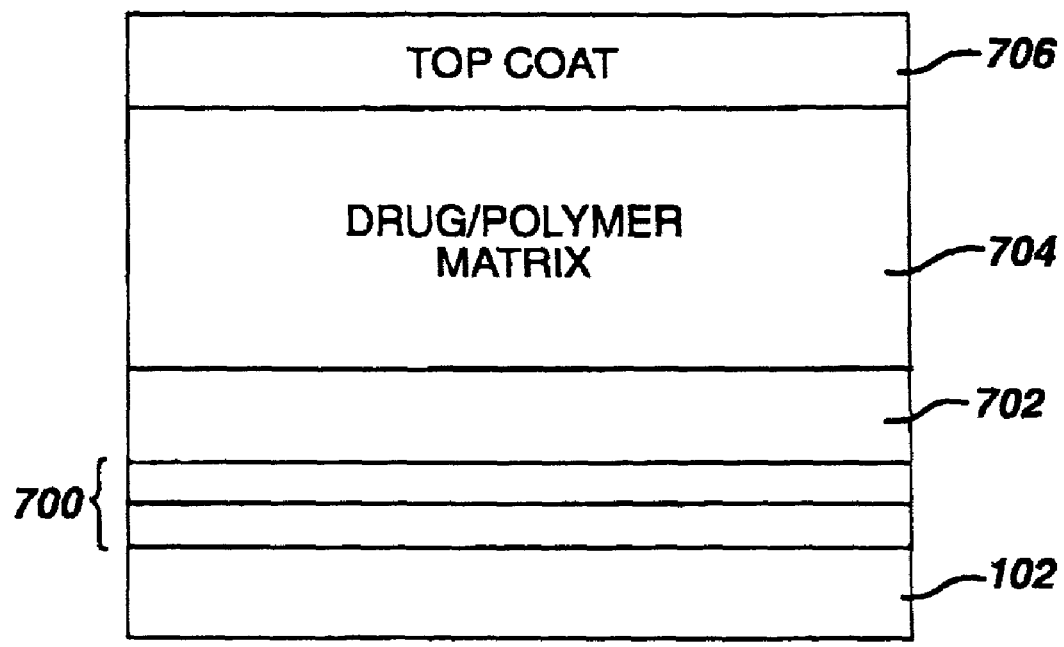
FIG. 23 is a cross-sectional view of a band of the stent in FIG. 1 having a modified polymer coating in accordance with the present invention.

In an alternate approach, physical and/or chemical cross-linking methods may be applied to improve the bond strength between the polymeric coating containing the drugs, agents or compounds and the surface of the medical device or between the polymeric coating containing the drugs, agents or compounds and a primer. Alternately, other primers applied by either traditional coating methods such as dip, spray or spin coating, or by RF-plasma polymerization may also be used to improve bond strength. For example, as shown in FIG. 23, the bond strength can be improved by first depositing a primer layer 700 such as vapor polymerized parylene-C on the device surface, and then placing a secondary layer 702 which comprises a polymer that is similar in chemical composition to the one or more of the polymers that make up the drug-containing matrix 704, e.g., polyethylene-co-vinyl acetate or polybutyl methacrylate but has been modified to contain cross-linking moieties. This secondary layer 702 is then cross-linked to the primer after exposure to ultraviolet light. It should be noted that anyone familiar with the art would recognize that a similar outcome could be achieved using cross-linking agents that are activated by heat with or without the presence of an activating agent. The drug-containing matrix 704 is then layered onto the secondary layer 702 using a solvent that swells, in part or wholly, the secondary layer 702. This promotes the entrainment of polymer chains from the matrix into the secondary layer 702 and conversely from the secondary layer 702 into the drug-containing matrix 704. Upon removal of the solvent from the coated layers, an interpenetrating or interlocking network of the polymer chains is formed between the layers thereby increasing the adhesion strength between them. A top coat 706 is used as described above.

A related difficulty occurs in medical devices such as stents. In the drug-coated stents crimped state, some struts come into contact with each other and when the stent is expanded, the motion causes the polymeric coating comprising the drugs, agents or compounds to stick and stretch. This action may potentially cause the coating to separate from the stent in certain areas. The predominant mechanism of the coating self-adhesion is believed to be due to mechanical forces. When the polymer comes in contact with itself, its chains can tangle causing the mechanical bond, similar to Velcro®. Certain polymers do not bond with each other, for example, fluoropolymers. For other polymers, however, powders may be utilized. In other words, a powder may be applied to the one or more polymers incorporating the drugs, agents or other compounds on the surfaces of the medical device to reduce the mechanical bond. Any suitable biocompatible material which does not interfere with the drugs, agents, compounds or materials utilized to immobilize the drugs, agents or compounds onto the medical device may be utilized. For example, a dusting with a water soluble powder may reduce the tackiness of the coatings surface and this will prevent the polymer from sticking to itself thereby reducing the potential for delamination. The powder should be water-soluble so that it does not present an emboli risk. The powder may comprise an anti-oxidant, such as vitamin C, or it may comprise an anti-coagulant, such as aspirin or heparin. An advantage of utilizing an anti-oxidant may be in the fact that the anti-oxidant may preserve the other drugs, agents or compounds over longer periods of time.

It is important to note that crystalline polymers are generally not sticky or tacky. Accordingly, if crystalline polymers are utilized rather than amorphous polymers, then additional materials may not be necessary. It is also important to note that polymeric coatings without drugs, agents, and/or compounds may improve the operating characteristics of the medical device. For example, the mechanical properties of the medical device may be improved by a polymeric coating, with or without drugs, agents and/or compounds. A coated stent may have improved flexibility and increased durability. In addition, the polymeric coating may substantially reduce or eliminate galvanic corrosion between the different metals comprising the medical device. The same holds true for anastomosis devices.

Any of the above-described medical devices may be utilized for the local delivery of drugs, agents and/or compounds to other areas, not immediately around the device itself. In order to avoid the potential complications associated with systemic drug delivery, the medical devices of the present invention may be utilized to deliver therapeutic agents to areas adjacent to the medical device. For example, a rapamycin coated stent may deliver the rapamycin to the tissues surrounding the stent as well as areas upstream of the stent and downstream of the stent. The degree of tissue penetration depends on a number of factors, including the drug, agent or compound, the concentrations of the drug and the release rate of the agent. The same holds true for coated anastomosis devices.

The drug, agent and/or compound/carrier or vehicle compositions described above may be formulated in a number of ways. For example, they may be formulated utilizing additional components or constituents, including a variety of excipient agents and/or formulary components to affect manufacturability, coating integrity, sterilizability, drug stability, and drug release rate. Within exemplary embodiments of the present invention, excipient agents and/or formulary components may be added to achieve both fast-release and sustained-release drug elution profiles. Such excipient agents may include salts and/or inorganic compounds such as acids/bases or buffer components, anti-oxidants, surfactants, polypeptides, proteins, carbohydrates including sucrose, glucose or dextrose, chelating agents such as EDTA, glutathione or other excipients or agents.

It is important to note that any of the above-described medical devices may be coated with coatings that comprise drugs, agents or compounds or simply with coatings that contain no drugs, agents or compounds. In addition, the entire medical device may be coated or only a portion of the device may be coated. The coating may be uniform or non-uniform. The coating may be discontinuous.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A device for joining substantially tubular organs in a living organism, comprising:
    an anastomosis device for connecting a graft vessel to a target vessel such that the two vessels are in fluid communication, the anastomosis device including a fastening flange and a plurality of staples connected to the fastening flange and having sharpened ends with barbs, the fastening flange comprising a single wire ring structure having a substantially sinusoidally shaped initial configuration for reduced profile delivery and a substantially flat profile final configuration post deployment, and the plurality of staples being configured to spring from a restraint position to a position substantially perpendicular to the ring structure and finally to an everted loop position through the graft vessel and target vessel, the plurality of staples extending from the wire ring structure in the same direction as the substantially sinusoidally shaped configuration and extending substantially beyond the wire ring for eversion;
    a primer layer affixed to at least a portion of the anastomosis device;
    a biocompatible vehicle affixed to the primer layer covering the at least a portion of the anastomosis device as a thin polymeric coating covering the elements of the device, wherein the biocompatible vehicle comprises a polyfluoro copolymer comprising polymerized residue of a first moiety comprising vinylidenefluoride, and polymerized residue of a second moiety comprising hexafluoropropylene and which is copolymerized with the first moiety, thereby producing the polyfluoro copolymer, wherein said polyfluoro copolymer comprises from about 55 to about 65 weight percent of the polymerized residue of the vinylidenefluoride copolymerized with from about 45 to about 35 weight percent of the polymerized residue of hexafluoropropylene, the primer layer and the polymer are similar in chemical composition with the primer layer being a diluted version of the polyfluoro copolymer, and wherein the weight of the biocompatible layer being about 0.4 to about 10 percent by weight;
    a rapamycin in therapeutic dosages incorporated into the biocompatible vehicle for the treatment of reactions by the living organism caused by the anastomosis device or the implantation thereof, the thin polymeric coating being configured to control the elution rate of the rapamycin into the surrounding tissue; and
    at least one top coating for delaying the release of the rapamycin.

* * * * *